United States Patent
Tamura

(10) Patent No.: US 8,114,391 B2
(45) Date of Patent: Feb. 14, 2012

(54) HAIR CARE COMPOSITION

(75) Inventor: Seiki Tamura, Kanagawa Prefecture (JP)

(73) Assignee: Dow Corning Toray Company, Ltd., Chiyoda-ku, Tokyo (JP)

( * ) Notice: Subject to any disclaimer, the term of this patent is extended or adjusted under 35 U.S.C. 154(b) by 1839 days.

(21) Appl. No.: 10/540,816

(22) PCT Filed: Dec. 24, 2003

(86) PCT No.: PCT/JP03/16566
§ 371 (c)(1), (2), (4) Date: Jun. 24, 2005

(87) PCT Pub. No.: WO2004/058198
PCT Pub. Date: Jul. 15, 2004

(65) Prior Publication Data
US 2006/0029559 A1    Feb. 9, 2006

(30) Foreign Application Priority Data
Dec. 26, 2002  (JP) ................................. 2002-376615

(51) Int. Cl.
A61Q 5/06 (2006.01)
A61Q 5/12 (2006.01)
C11D 1/62 (2006.01)

(52) U.S. Cl. .................................. 424/70.12; 424/70.28

(58) Field of Classification Search ............... None
See application file for complete search history.

(56) References Cited

U.S. PATENT DOCUMENTS

| | | | |
|---|---|---|---|
| 5,286,476 A | 2/1994 | Nanba et al. | |
| 5,620,684 A | 4/1997 | Dupuis | |
| 5,935,587 A | 8/1999 | Cauwet et al. | |
| 6,187,891 B1 * | 2/2001 | Rautschek et al. | 528/25 |

FOREIGN PATENT DOCUMENTS

| | | |
|---|---|---|
| EP | 0 492 657 | 12/1991 |
| JP | 63-183517 | 7/1988 |
| JP | 63-243018 | 10/1988 |
| JP | 4-211605 | 8/1992 |
| JP | 8-188519 | 7/1996 |
| JP | 8-208439 | 8/1996 |
| JP | 9-59132 | * 3/1997 |
| JP | 11-79956 | * 3/1999 |
| JP | 2002-179535 | 6/2002 |

OTHER PUBLICATIONS

English language Abstract for JP 9-59132 extracted from espacenet.com database dated Nov. 1, 2005.
English language Abstract for JP 11-79956 extracted from espacenet.com database dated Nov. 1, 2005.
English language Abstract for JP 63-183517 extracted from espacenet.com database dated Jun. 13, 2005.
English language Abstract for JP 8-188519 extracted from espacenet.com database dated Jun. 13, 2005.
English language Abstract for JP 8-208439 extracted from espacenet.com database dated Jun. 13, 2005.
English language Abstract for JP 2002-179535 extracted from espacenet.com database dated Jun. 13, 2005.

* cited by examiner

*Primary Examiner* — David J Blanchard
*Assistant Examiner* — Lori K Mattison
(74) *Attorney, Agent, or Firm* — Howard & Howard Attorneys PLLC

(57) ABSTRACT

(1) The invention provides a composition for hair that imparts to the hair such properties as moist feeling, the feel of smoothness, thick-film touch, and ease of combing. These properties are long lasting and do not disappear after repeated brushing. Furthermore, neither in a moist state during washing, nor in a dry state, the hair produces the feel of unpleasant touch. The hair treated with the composition of the invention does to become sticky after drying. (2) The shampoo compositions of the invention demonstrate superb foamability and washability. The feel of smoothness and ease of combing are not lost even after the repeated hair wash. The composition of the invention comprises a specific block copolymer of polyorganosiloxane and polyoxyalkylene used in the amount of 0.01 to 10 mass %.

12 Claims, No Drawings

HAIR CARE COMPOSITION

TECHNICAL FIELD

The present invention relates to a composition for hair that contains a specific block copolymer.

BACKGROUND ART (1) To obtain a composition for hair that imparts to the hair excellent luster, smooth touch, and protection against damages such as hair splitting or breaking, it was proposed to use a composition that contains dimethylpolysiloxane and/or methylphenylpolysiloxane of a high molecular weight (with a degree of polymerization within the range of 3,000 to 20,000) (see, e.g., Japanese Unexamined Patent Application Publication (hereinafter referred to as "Kokai") S63-183517 and Kokai S63-243018).

However, the effects of imparting to hair such properties as luster, smooth touch, and protection against damage obtained with the use of the aforementioned composition do not last long and are lost (or diminished) after brushing or drying.

Furthermore, the aforementioned composition cannot impart to hair a sufficient moist feeling and thick-film touch (here and hereinafter, the feeling that the hair coat is thick and moist).

The moist feeling is lost also when the hair treated with the aforementioned compositions is in a dry or wet state.

(2) In order to impart to hair an antistatic effect, facilitate combing, and provide the moisture feeling, it was suggested to use a composition for hair that contains a block copolymer composed of a polyorganosiloxane block with the average molecular weight within the range of 400 to 10,000 and a polyoxyalkylene block with the average molecular weight within the range of 300 to 10,000 (see, e.g., Kokai H04-211605).

However, the aforementioned composition is unable to impart to hair a sufficient feel of smoothness. Moreover, the positive effects imparted to hair by the composition also cannot last long and are lost (or diminished) after the hair is brushed or dried.

Furthermore, as the aforementioned composition could not form a sufficiently thick coating film on the surface of the hair, it could not provide the thick-film touch.

When hair treated with the aforementioned composition becomes dry, it produces the feel of unfavorable touch and tackiness.

(3) To obtain a composition for hair with which the hair is provided with an excellent gloss, moist touch, smooth feeling, smoothness in repeated washing and smoothness in repeated use, is prevented from being damaged, protected against chemical and mechanical treatment, and maintains the above-listed effects for many hours, it was proposed to use a reactive silicone-type block copolymer composed of a polyorganosiloxane block, amino-modified polyorganosiloxane block, and a polyoxyalkylene block (see, e.g., Kokai 2002-179535).

However, the last-mentioned composition produces an unfavorable feeling to the touch when hair is in a wet state and cannot produce good feeling in hair washing.

Furthermore, since this composition cannot form a sufficiently thick coating layer on the surface of hair, it also cannot impart to hair a thick-film touch.

DISCLOSURE OF INVENTION

Problems to be Solved by the Present Invention

The present invention is aimed at a solution of the problems described above.

More specifically, it is an object of the present invention to provide a composition for hair that is capable of imparting to hair a moist feeling, a feel of smoothness, ease of combing, moist feeling and smoothness even after repeated brushing and drying, and preserving a favorable touch, irrespective of whether the hair is in a dry or a wet state.

It is another object of the invention to provide a composition for hair that does not produce a sticking sensation after the hair is dried.

It is a further object of the invention to provide a composition for hair that is capable of coating the hair with a sufficiently thick coating layer, thus imparting to hair a thick-film touch.

It is another object of the invention to provide a composition for hair that imparts to hair excellent washing and foaming properties and maintains good feel of smoothness and ease of combing, even after repeated hair washing.

Means for the Solution of the Problems

The composition for hair that relates to the present invention [hereinafter referred to as "composition" or "composition of the present invention"] is characterized by comprising a block copolymer represented by the following general formula (1):

General formula (1)

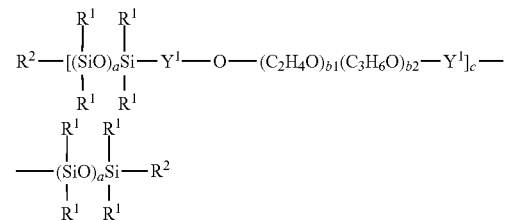

[wherein $R^1$ independently designates univalent hydrocarbon groups free of aliphatic unsaturation, hydroxyl groups, or alkoxy groups;

$Y^1$ designates a bivalent organic group;

$R^2$ independently designates hydrogen atoms, hydroxyl groups, substituted or unsubstituted univalent hydrocarbon groups, alkoxy groups, or groups represented by the following formula:

$$-Y^1-O-(C_2H_4O)_{b1}(C_3H_6O)_{b2}-Y^2$$

(wherein $Y^2$ is a hydrogen atom or a substituted or unsubstituted univalent hydrocarbon group);

"a" is 1 or a greater integer;

"b1" is 1 or a greater integer;

"b2" is 0, 1 or a greater integer;

"c" is 1 or a greater integer;

the average molecular weight of the polyorganosiloxane block represented by formula:

$$-(SiR^1{}_2O)_aSiR^1{}_2-$$

is equal to or exceeds 10,500; the aforementioned polyorganosiloxane block constitutes 50 to 99 mass % of block copolymer (A);

the average molecular weight of the polyoxyalkylene block represented by formula:

$$-(C_2H_4O)_{b1}(C_3H_6O)_{b2}-$$

is within the range of 130 to 10,000; and the average molecular weight of aforementioned block copolymer (A) is equal to or higher than 50,000].

The composition of the invention may be embodied as follows:

[1] The content of aforementioned block copolymer (A) is within the range of 0.01 to 10 mass %.

[2] The composition may additionally contain a block copolymer (B) of at least one type represented by general formula (2) given below with the content within the range of 0.01 to 10 mass % (per total weight of the composition as a reference):

General formula (2)

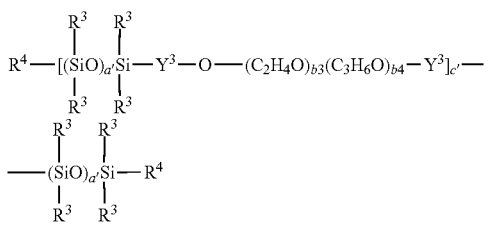

[wherein $R^3$ independently designates substituted or unsubstituted univalent hydrocarbon groups or groups of the following formula:

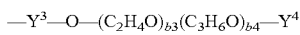

(wherein $Y^3$, b3, and b4 are defined below, $Y^4$ designates hydrogen atoms or a substituted or unsubstituted univalent hydrocarbon group);

$Y^3$ designates a bivalent organic group;

$R^4$ independently designates hydrogen atoms, hydroxyl groups, substituted or unsubstituted univalent hydrocarbon groups, alkoxy groups, or groups represented by the following formula:

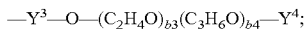

"a'" is an integer within the range of 1 to 1350;

"b3" and "b4", respectively, are integers within the range of 0 to 220 (but b3 and b4 cannot be both 0);

"c'" is an integer within the range of 0 to 50; when "c'" is 0, at least one of the groups designated by $R^3$ or $R^4$ is represented by the formula:

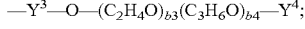

the average molecular weight of the polyorganosiloxane block represented by formula:

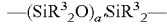

is within the range of 134 to 10,000;

the aforementioned polyorganosiloxane block constitutes 0.7 to 97.5 mass % of block copolymer (B);

the average molecular weight of the polyoxyalkylene block represented by formula:

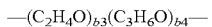

is within the range of 130 to 10,000; and the average molecular weight of aforementioned block copolymer (B) is within the range of 650 to 100,000].

[3] The composition may further contain a silicone compound (C) of at least one type expressed by below-given general formula (3) and contained in an amount of 0.01 to 10 mass % (per total weight of the composition as a reference).

[4] In below-given formula (3) for silicone compound (C), $Z^1$ designates an amino-containing group or an ammonium-containing group; when "r"=0, at least one $R^8$ becomes $X^1$:

General formula (3)

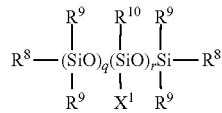

[In the above formula, $R^9$ independently designates hydrogen atoms and substituted or unsubstituted univalent hydrocarbon groups; $X^1$ designates a reactive functional group represented by formula:

(wherein $R^{11}$ is a direct bond or a bivalent hydrocarbon group with 1 to 20 carbon atoms, and $Z^1$ is a group that contains a reactive group); $R^8$ are independently hydrogen atoms, hydroxyl groups, substituted or unsubstituted univalent hydrocarbon groups, alkoxy groups, or groups represented by $X^1$; $R^{10}$ represents either $R^9$ or $X^1$; "q" is an integer that may be at least 1; "r" is 0 or an integer that may be at least 1; the average molecular weight of component (C) is within the range of 250 to 1,000,000.]

[5] The composition may further contain a cationic surface-active agent (D) of at least one type comprising any of the compounds represented by the below-given general formulae (4), (5), and (6):

General formula (4)

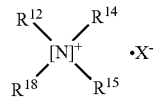

General formula (5)

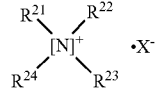

General formula (6)

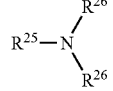

[where in general formula (4), $R^{12}$ designates an alkyl group with 10 to 24 carbon atoms, hydroxyalkyl groups, acyloxyalkyl groups bonded to alkyl groups with 10 to 24 carbon atoms, or amidoalkyl groups; $R^{14}$ and $R^{15}$ independently designate benzyl groups, hydroxyalkyl groups, or alkyl groups having 1 to 3 carbon atoms; $R^{13}$ may be $R^{12}$, $R^{14}$, or $R^{15}$; and X designates a halogen atom or an alkyl sulfuric acid group.

In general formula (5), at least one of $R^{21}$, $R^{22}$, $R^{23}$, and $R^{24}$ designates an aliphatic acryloxy (polyethoxy) ethyl group, alkenyl group, and a linear or branched alkyl group that contain 8 to 35 of total carbon atoms and can be OH-substituted or cleaved by functional groups of the following formulae: —O—, —CONH—, —OCO—, or —COO—. The remaining groups may comprise hydroxyalkyl or alkyl groups with 1 to 5 carbon atoms, or polyoxyethylene groups with the total addition number not exceeding 10; $X^-$ designates a halogen ion or an organic anion.

In general formula (6), $R^{25}$ designates an alkenyl group and a linear or branched alkyl group that contains 8 to 35 of total carbon atoms and can be OH-substituted or cleaved by functional groups of the following formulae: —O—, —CONH—, —OCO—, or —COO—. $R^{26}$ independently designates a hydroxyalkyl group, alkenyl group, or alkyl group with 1 to 22 carbon atoms.]

[6] The composition may further contain a surface-active agent (E) of at least one type selected from an anionic surface-active agent, amphoteric surface-active agent, and nonionic surface-active agent, said agent being used in an amount of 0.01 to 40 mass % (per total weight of the composition as a reference).

[7] The composition may further contain a water-soluble polymer (F) of at least one type added in an amount of 0.01 to 10 mass % (per total weight of the composition as a reference).

[8] The aforementioned block copolymer (A) may be dissolved in a liquid cyclic silicone (G).

[9] The aforementioned block copolymer (A) may be dissolved in a liquid chain silicone (H).

[10] The aforementioned block copolymer (A) may be dissolved in a liquid isoparaffin-type hydrocarbon (I).

[11] The aforementioned block copolymer (A) may be dissolved in a liquid or solid ester oil (J).

[12] The composition may further contain an emulsion obtained by emulsifying the solution formed by dissolving said block copolymer (A) (an emulsion-type composition).

[13] In case of emulsification, the emulsion can be further compounded with 0.01 to 10 mass % (per total mass of the composition as a reference) of a water-soluble polyhydric alcohol (K).

DETAILED DESCRIPTION OF THE INVENTION

The invention will now be described in more detail.

The composition of the invention contains a block copolymer (A) of aforementioned general formula (1) as an indispensable component.

<Block Copolymer (A)>

In aforementioned general formula (1) that represents block copolymer (A), $R^1$ independently designates univalent hydrocarbon groups free of aliphatic unsaturation, hydroxyl groups, or alkoxy groups.

The univalent hydrocarbon groups free of aliphatic unsaturation may be exemplifies by methyl, ethyl, propyl, butyl, octyl, dodecyl, phenyl, phenethyl, etc. The methyl and phenyl groups are preferable.

The alkoxy groups designated by $R^1$ may be exemplified by alkoxy groups with 1 to 12 carbon atoms, preferably, 1 to 8 carbon atoms, and even more preferably, 1 to 6 carbon atoms, such as methoxy, ethoxy, propoxy, butoxy, isopropenyloxy, methoxyethoxy, phenyloxy, acetoxy, cyclohexyloxy, and dodecanyloxy groups. The methoxy and ethoxy groups are preferable.

The bivalent organic groups that are represented by $Y^1$ in aforementioned formula (1) are bonded to the silicon atom of the polyorganosiloxane block via a carbon-silicon bond and with the polyoxyalkylene block [poly(oxyethylene) (oxypropylene) block] via an oxygen atom.

The following are specific examples of organic groups designated by $Y^1$: —$R^{16}$—, —$R^{16}$—CO—, —$R^{16}$—NHCO—, —$R^{16}$—NHCONHR$^{17}$—NHCO—, and —$R^{16}$—OOCNH—$R^{17}$—NHCO— [where $R^{16}$ designates ethylene, propylene, butylene, or similar alkylene groups, and $R^{17}$ designates alkylene groups, —$C_6H_4$—, —$C_6H_4$—$C_6H_4$—, —$C_6H_4$—$CH_2$—$C_6H_4$—, —$C_6H_4$—$CH(CH_3)$—$C_6H_4$—, or similar arylene groups].

The following are preferable organic groups designated by $Y^1$: —$CH_2CH_2$—, —$CH_2CH_2CH_2$—, —$CH_2CH(CH_3)$ $CH_2$—, —$(CH_2)_4$—, —$(CH_2)_2CO$—, —$(CH_2)_3NHCO$—, —$(CH_2)_3NHCONHC_6H_4CO$—, and —$(CH_2)_3$ $OOCNHC_6H_4NHCO$—. Most preferable of the above groups are —$CH_2CH_2$—, —$CH_2CH_2CH_2$—, —$CH_2CH(CH_3)$ $CH_2$—, especially —$CH_2CH(CH_3)CH_2$—.

In the above formula (1), $R^2$ independently designates hydrogen atoms, hydroxyl groups, substituted or unsubstituted univalent hydrocarbon groups, alkoxy groups, or groups represented by the following formula:

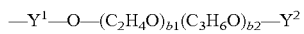

(wherein $Y^2$ is a hydrogen atom or a substituted or unsubstituted univalent hydrocarbon group; $Y^1$ is the same as defined above).

Substituted or unsubstituted univalent hydrocarbon groups designated by $R^2$ can be represented by alkyl groups with 1 to 12 carbon atoms, preferably, 1 to 8 carbon atoms, and more preferably, 1 to 6 carbon atoms, such as methyl, ethyl, propyl, aminopropyl, glycidoxypropyl, butyl, pentyl, hexyl, octyl, and dodecyl groups; alkenyl groups with 2 to 8 carbon atoms, preferably 2 to 6 carbon atoms, such as vinyl, propenyl, butenyl, pentenyl, hexenyl, and octenyl groups; cycloalkyl groups with 3 to 8 carbon atoms, preferably 5 to 7 carbon atoms, such as cyclopropyl, cyclopentyl, and cyclohexyl groups; halogenated alkyl groups with 1 to 8 carbon atoms, preferably 1 to 6 carbon atoms, such as trifluoropropyl, perfluorooctylethyl, chloropropyl, and pentachlorooctyl groups; aliphatic acyl groups with 1 to 18 carbon atoms, preferably 1 to 7 carbon atoms, such as acetyl, propionyl, pentanoyl, and octanoyl groups; aromatic acyl groups with 7 to 15 carbon atoms, preferably 7 to 11 carbon atoms, such as benzoyl and benzylcarbonyl groups; aryl groups with 6 to 14 carbon atoms, preferably 6 to 10 carbon atoms, such as phenyl, tolyl, xylyl, and naphthyl groups; as well as aralkyl groups with 7 to 15 carbon atoms, preferably 7 to 11 carbon atoms, such as benzyl and phenethyl groups. Most preferable are methyl and phenyl groups.

In the groups represented by formula:

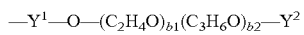

(i.e., the groups that can be represented by $R^2$), $Y^2$ is a hydrogen atom or a substituted or unsubstituted univalent hydrocarbon group. The substituted or unsubstituted univalent hydrocarbon group designated by $Y^2$ may be exemplified by the same groups as given above for $R^2$.

The most preferable groups designated by $Y^2$ are the following: alkenyl group, such as —CH=$CH_2$, —$CH_2CH$=$CH_2$, —$CH_2C(CH_3)$=$CH_2$, —$(CH_2)_2$— CH=$CH_2$, hydroxyl groups, acetyl groups, and alkyl groups with 1 to 12 carbon atoms.

In aforementioned formula (1), "a" is an integer equal to or greater than 1, preferably an integer within the range of 140 to 1350, and even more preferably, within the range of 160 to 400.

"b1" is an integer equal to or greater than 1, preferably an integer within the range of 3 to 220, and even more preferably, within the range of 7 to 60.

"b2" is 0 or an integer equal to or greater than 1, preferably an integer within the range of 0 to 170, and even more preferably, within the range of 0 to 50.

"c" is an integer equal to or greater than 1, preferably an integer within the range of 5 to 50, and even more preferably, within the range of 10 to 50.

The average molecular weight of the polyorganosiloxane block represented by formula:

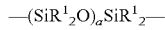

is equal to or exceeds 10,500, and should be preferably within the range of 10,500 to 100,000, more preferably, within the range of 12,000 to 30,000, and even more preferably, within the range of 14,000 to 25,000.

If the composition for hair is comprised a block copolymer where the average molecular weight of the polyorganosiloxane block is below 10,500, it will be impossible to impart to hair sufficient feel of smoothness and thick-film touch. Furthermore, the effects of imparting to hair the above properties will not last long and will be lost (diminished) after brushing and drying. When the hair treated with the composition having the average molecular weight below the indicated limit becomes dry, it will produce the feel of unfavorable touch and tackiness.

In block copolymer (A), the total content (total weight) of the aforementioned polyorganosiloxane block constitutes 50 to 99 mass %, preferably 70 to 99 mass %, and even more preferably, 90 to 99 mass %.

If the composition for hair cosmetic is comprised of a block copolymer where the content of the polyorganosiloxane-block is below 50 mass %, it will be impossible to impart to hair sufficient luster and feel of smoothness. Furthermore, after drying, the hair will become sticky.

On the other hand, if the composition for hair cosmetic is comprised of the block copolymer where the content of the aforementioned block exceeds 99 mass %, this will not allow maintaining glossiness and the feel of smoothness over a long period of time and restrict the effects of moist feeling and sensation of thick-film touch.

The average molecular weight of the polyoxyalkylene block represented by formula:

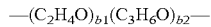

is within the range of 130 to 10,000, preferably, within the range of 310 to 5,000, and even more preferably, 440 to 3,000.

If the composition for hair is comprised of the aforementioned block copolymer where the average molecular weight of the polyoxyalkylene block is below 130, the long-lasting effect of smoothness will be obtained, but the effects of moist feeling and sensation of thick-film touch, as well as diminishing of the sensation of unfavorable touch will be insufficient.

On the other hand, if the composition for hair is comprised of a block copolymer where the average molecular weight of the polyoxyalkylene block exceeds 10,000, it will be possible to provide sufficient effects of imparting to hair a moist feeling and to diminish the sensation of unfavorable touch, but the effects of smoothness will be insufficient, and after drying the hair may develop the feel of sticking.

The oxyethylene group ($—C_2H_4O—$) and the oxypropylene group ($—C_3H_6O—$) used in the polyoxyalkylene block of block copolymer (A) may be bonded at random or in block form.

It is recommended that, in the above formula that shows the preferable polyoxyalkylene block, the repetition number (b1/b2) be within the range of (3 to 220)/(0 to 170), preferably, (7 to 60)/(0 to 50), and even more preferably, (10 to 35)/(0 to 35).

The block copolymer (A) should have the average molecular weight above 50,000, preferably within the range of 100,000 to 2,000,000, and even more preferably, within the range 150,000 to 1,000,000.

If the composition for hair comprises the aforementioned block copolymer with the average molecular weight below 50,000, it will be difficult to impart to hair the feel of smoothness, thick-film touch, and moist feeling. Moreover, it will be difficult to diminish the feel of unfavorable touch and tackiness after drying.

In the composition of the invention, the content of the block copolymer (A) should be within the range of 0.01 to 10 mass %, preferably 0.05 to 5 mass %, and even more preferably, 0.1 to 3 mass %.

If the content of the aforementioned block copolymer is below the lower recommended limit, it will be impossible to achieve the object of the present invention. If, on the other hand, the block copolymer is used in excess, this will decrease its solubility.

<Block Copolymer (B)>

Block copolymer (B) is an optional component of the composition of the invention. It is a copolymer of polyorganosiloxane and polyoxyalkylene represented by aforementioned formula (2).

By using aforementioned block copolymer (A) in combination with block copolymer (B), it becomes possible to improve the effects produced by block copolymer (A) (especially, the effect of imparting a moist feeling).

In aforementioned formula (2) of block copolymer (B), $R^3$ independently designates substituted or unsubstituted univalent hydrocarbon groups or groups of the following formula:

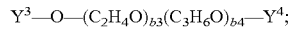

(wherein $Y^3$, b3, and b4 are defined below, $Y^4$ designates hydrogen atoms or a substituted or unsubstituted univalent hydrocarbon group); $Y^3$ designates a bivalent organic group; $R^4$ independently designates hydrogen atoms, hydroxyl groups, substituted or unsubstituted univalent hydrocarbon groups, alkoxy groups, or groups represented by the following formula:

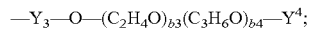

When in the aforementioned formula (2) the repetition number "c'" is 0, then $R^3$ or $R^4$ is represented by one formula:

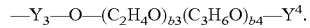

Specific examples of substituted or unsubstituted univalent hydrocarbon groups represented in formula (2) by $R^3$, $R^4$, and $Y^4$ may be the same groups as given above for $R^2$ of aforementioned formula (1). Most preferable of these groups are methyl and phenyl groups.

In aforementioned general formula (2), the bivalent organic groups designated by $Y^3$ can be exemplified by the same groups that were shown above for $Y^1$ of formula (1).

In aforementioned formula (2), "a'" is an integer within the range of 1 to 1350, preferably within the range of 1 to 100, and even more preferably, within the range of 1 to 50.

"b3" is an integer within the range of 0 to 220, preferably within the range of 3 to 60, and even more preferably, within the range of 5 to 50, and even further preferably, within the range of 7 to 35.

"b4" is an integer within the range of 0 to 220, preferably within the range of 0 to 60, and even more preferably, within the range of 3 to 45, and even further preferably, within the range of 5 to 35.

"b3" and "b4" cannot be both 0.

"c'" is an integer within the range of 0 to 50, preferably within the range of 0 to 20, and even more preferably, within the range of 0 to 10.

In block copolymer (B), the average molecular weight of the polyorganosiloxane block represented by formula:

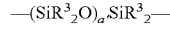

is within the range of 134 to 10,000, preferably within the range of 134 to 5,000, and even more preferably, within the range of 800 to 3,500.

In block copolymer (B), the total content (total weight) of aforementioned polyorganosiloxane block constitutes 0.7 to 97.5 mass %, preferably 10 to 90 mass %, and even more preferably, 20 to 80 mass %.

The average molecular weight of the polyoxyalkylene block represented in block copolymer (B) by formula:

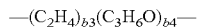

should be within the range of 130 to 10,000, preferably within the range of 310 to 5,000, and even more preferably, within the range of 440 to 3,000.

The average molecular weight of block copolymer (B) is maintained within the range of 650 to 100,000, preferably, 1,000 to 70,000, and even more preferably, 3,000 to 50,000.

In the composition of the invention, the content of block copolymer (B) should be within the range of 0.01 to 10 mass %, preferably within the range of 0.05 to 5 mass %, and even more preferably, within the range of 0.1 to 3 mass %.

If the content of block copolymer (B) is below 0.01 mass %, the presence of this block copolymer will not produce any effect. If, on the other hand, the content exceeds the recommended upper limit, this will decrease solubility of block copolymer (B).

<Silicone Compound (C)>

Silicone compound (C) can be added to the composition of the invention as an optional compound. It is a reactive silicone compound that is represented by aforementioned general formula (3).

Coexistence of component (A) with component (C) improves effects of block copolymer (A) (especially, glossiness and feel of smoothness).

In aforementioned formula (3), the bivalent hydrocarbon group ($R^{11}$) with 1 to 20 carbon atoms that are included into the structure of reactive functional group $X^1$ of formula (3) may be represented by —$CH_2$—, —$CH_2CH_2$—, —$CH_2CH_2CH_2$—, —$CH(CH_3)CH_2$—, —$(CH_2)_4$—, —$(CH_2)_6$—, —$(CH_2)_8$—, —$CH_2CH_2C_6H_4$—, —$(CH_2)_{12}$—, —$(CH_2)_{16}$—. The most preferable are propylene groups.

The following groups can be selected as groups ($Z^1$) that contain reactive groups and are included into the structure of reactive function group ($X^1$): epoxy, amino, ammonium, hydroxyl, carboxyl, acyl, mercapto, methacrylic, isocyanate, ureido, vinyl, amido, imido, imino, aldehydo, nitro, nitrile, oxyme, azo, hydrazone, alkoxy, alkoxysilyl groups, etc.

The following are specific examples of reactive functional groups ($X^1$): —$(CH_2)_3OH$, —$(CH_2)_3SH$, —$(CH_2)_3NH_2$, —$(CH_2)_3NH(CH_2)_2NH_2$, —$(CH_2)_3N(CH_3)_2$, —$(CH_2)_3N(CH_3)(CH_2)_2N(CH_3)_2$, —$(CH_2)_3N^+(CH_3)_3Cl^-$, —$(CH_2)_3N(CH_3)(CH_2)_2N(CH_3)C=O(CH_3)$, —$(CH_2)_7COOH$, —$(CH_2)_3OCH_2CH(O)CH_2$, —$(CH_2)_3OC(=O)CH(CH_3)=CH_2$, —$(CH_2)_2Si(OCH_3)_3$, —$(CH_2)_2Si(OCH_2CH_3)_3$. The most preferable among the above are —$(CH_2)_3NH_2$, —$(CH_2)_3NH(CH_2)_2NH_2$, —$(CH_2)_3N(CH_3)_2$, —$(CH_2)_3N(CH_3)(CH_2)_2N(CH_3)_2$, and —$(CH_2)_3N^+(CH_3)_3Cl^-$.

Specific examples of substituted or unsubstituted univalent hydrocarbon groups designated in aforementioned general formula (3) by $R^8$, $R^9$, and $R^{10}$ are the same as groups given above for $R^2$ in general formula (1). Most preferable among these groups are methyl and phenyl groups.

In the composition of the invention, the content of silicone compound (C) should normally be within the range of 0.01 to 10 mass %, preferably 0.05 to 5 mass %, and even more preferably, 0.1 to 3 mass %.

If silicone compound (C) is contained in the amount less than 0.01 mass %, the presence of this compound will not produce any effect. If, on the other hand, silicone compound (C) is used in excess, this will decrease solubility of compound (C).

<Cationic Surface-Active Agent (D)>

Cationic surface-active agent (D) that is used in the composition of the invention as an optional component is the one represented by any of aforementioned general formulae (4), (5) and (6) (tertiary or quaternary ammonium salt).

The presence of cationic surface-active agent (D) improves effects of block copolymer (A) (especially suppression of unfavorable touch) and imparts to the hair so-called rinse effects (feel of smoothness, luster, and ease of combing).

In case the group designated in aforementioned general formula (4) by $R^{12}$ is an alkyl group with 10 to 24 carbon atoms, it can be represented by the following specific examples: cetyl group, lauryl group, stearyl group, and behenyl group.

In case the group designated by $R^{12}$ is a hydroxyalkyl group with 10 to 24 carbon atoms, it can be exemplified by a 12-hydroxystearyl group.

In case the group designated by $R^{12}$ is an acyloxyalkyl group bonded to alkyl group with 10 to 24 carbon atoms, it can be exemplified by stearylacyloxyethyl.

In case the group designated by $R^{12}$ is an amidoalkyl group bonded to alkyl group with 10 to 24 carbon atoms, it can be exemplified by lanolin fatty acid aminopropyl group.

Preferable groups designated by $R^{12}$ are alkyl groups with 14 to 22 carbon atoms and, especially, stearyl and behenyl groups.

Preferable groups that in aforementioned general formula (4) are designated by $R^{14}$ and $R^{15}$ may be represented by methyl, ethyl, propyl, hydroxymethyl, and hydroxyethyl groups.

The groups designated in aforementioned formula (4) by $R^{13}$ may be the same as any of the groups designated by $R^{12}$, $R^{14}$, and $R^{15}$. Groups of $R^{13}$, $R^{14}$, and $R^{15}$ may be identical or different.

In aforementioned formula (4), preferable halogen atoms designated by "X" are atoms of chlorine and bromine.

The following are specific examples of cationic surface-active agents (D) composed of compounds represented by aforementioned general formula (4): cetyl trimethyl ammonium chloride, stearyl trimethyl ammonium chloride, behenyl trimethyl ammonium chloride, behenyl dimethyl hydroxyethyl ammonium chloride, stearyl dimethylbenzyl ammonium chloride, distearyl dimethyl ammonium chloride, lauryl trimethyl ammonium chloride, myristyl dimethyl benzyl ammonium chloride, lanolin fatty acid aminopropyl ethyldimethyl ammonium ethylsulfate, and cetyl triethyl ammonium methylsulfate. These compounds can be used individually or in combinations.

Most preferable of the above compounds are stearyl trimethyl ammonium chloride, behenyl trimethyl ammonium chloride, stearyl dimethylbenzyl ammonium chloride, and mixtures of these compounds.

In the compounds of formula (5), one, two, or three of the groups designated by $R^{21}$, $R^{22}$, $R^{23}$, and $R^{24}$ that may contain 8 to 35 of total carbon atoms (preferably 8 to 26 carbon atoms) can be OH-substituted or cleaved by functional group of the following formulae:—O—, —CONH—, —OCO—, or —COO—. The aforementioned groups designated by $R^{21}$, $R^{22}$, $R^{23}$, and $R^{24}$ may comprise linear or branched alkyl groups, alkenyl groups, or aliphatic acryloxy(polyethoxy) ethyl groups (hereinafter referred to as long-chained groups), the remaining groups are alkyl groups or hydroxyalkyl groups with 1 to 5 carbon atoms, or polyoxyethylene groups with the total addition mole number not exceeding 10; X⁻ designates a halogen ion or an organic anion.

The following are examples of compounds having one long-chained group among $R^{21}$, $R^{22}$, $R^{23}$, and $R^{24}$: stearyl trimethyl ammonium chloride, hydroxystearyl methyl ammonium chloride, capryl trimethyl ammonium chloride, myristyl trimethyl ammonium chloride, cetyl trimethyl ammonium chloride, cetyl trimethyl ammonium bromide, behenyl trimethyl ammonium chloride, lauryl trimethyl ammonium chloride, N-stearyl-N,N,N-tri(polyoxyethylene) ammonium chloride (total 3 mole added), etc.

The following are examples of compounds having two long-chained groups among $R^{21}$, $R^{22}$, $R^{23}$, and $R^{24}$: distearyl dimethyl ammonium chloride, di-hydrogenated-tallow dimethyl ammonium chloride, di-tallow dimethyl ammonium bromide, dioleyl dimethyl ammonium chloride, dipalmityl methylhydroxyethyl ammonium methosulfate, distearyl diethyl ammonium chloride, diisostearyl dimethyl ammonium methosulfate, di[(2-dodecanoylaamino)ethyl]dimethyl ammonium chloride, di[(2-stearoylamino)propyl]dimethyl ammonium ethosulfate, etc.

The following are examples of compounds having three long-chained groups among $R^{21}$, $R^{22}$, $R^{23}$, and $R^{24}$: dioleyl monostearyl methyl ammonium chloride, dioleyl monobehenyl methyl ammonium chloride, trioleyl methyl ammonium chloride, tristearyl methyl ammonium methosulfate, etc.

In addition to the above, the aforementioned compounds may be exemplified by branch-chained quaternary ammonium salts represented by below-given general formula (5A) or (5B), and by quaternary ammonium salts represented by below-given general formula (5C).

General formula (5A):

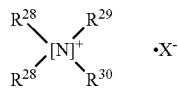   ·X⁻

General formula (5B):

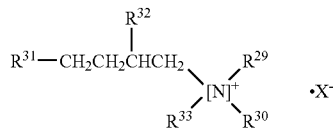   ·X⁻

[in the above formula, $R^{28}$ may designate a mixture of (a) a branched alkyl group represented by formula:

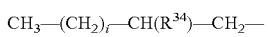

(wherein $R^{34}$ is a methyl or ethyl group, and "i" is an integer that has a total number of carbon atoms in the alkyl group that is within the range of 8 to 16); and
(b) a linear alkyl groups represented by formula:

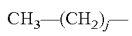

(wherein "j" is an integer within the range of 7 to 15, with the proviso that the branch chain index [(a)/[(a)+(b)]] should be within the range of 10 to 100 mole %.
$R^{29}$ and $R^{30}$ designate alkyl or hydroxyalkyl groups with 1 to 3 carbon atoms.
$R^{31}$ and $R^{32}$ designate alkyl groups with 2 to 12 carbon atoms.
$R^{33}$ designates group represented by formula:

or an alkyl group with 1 to 3 carbon atoms. X⁻ has the same meaning as defined above.]

General formula (5C)

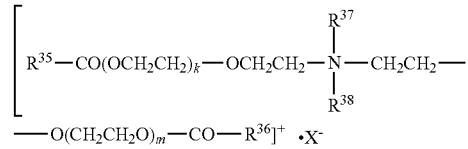

[In the above formula, $R^{35}$ and $R^{36}$ designate alkyl or alkenyl groups with 8 to 22 carbon atoms that can be substituted with hydroxysilyl groups. $R^{37}$ and $R^{38}$ designate $-(CH_2CH_2O)_p$H (where "p" is a number between 1 to 6) or alkyl groups with 1 to 3 carbon atoms. "k" and "m" are numbers from 0 to 5; X⁻ has the same meaning as defined above.]

The following are specific examples of X⁻ which is a counter ion of the aforementioned quaternary ammonium salts: a chlorine, iodine, bromine, or similar halogen ion; methosulfate, ethosulfate, methophosphate, ethophosphate, or a similar organic anion.

Among the above, the branch-chained quaternary ammonium salts represented by aforementioned general formula (5A) are normally synthesized by using an oxoalcohol with 8 to 16 carbon atoms as a starting material. Such salts can be exemplified by dialkyl dimethyl ammonium salt having an alkyl group and derived from oxoalcohol, dialkyl methyl hydroxyethyl ammonium salts, etc.

According to the present invention, the branch chain index of $R^{28}$ in aforementioned general formula (5A) should be normally kept within the range of 10 to 100 mole %, preferably 10 to 50 mole %. The total number of carbon atoms in $R^{28}$ should be within the range of 8 to 16, but for maintaining stability of distribution, the following distribution pattern is recommended: $C_8$ to $C_{11}$: below 5 mole %; $C_{12}$: 10 to 35 mole %; $C_{13}$: 15 to 40 mole %; $C_{14}$: 20 to 45 mole %; $C_{15}$: 5 to 30 mole %; $C_{16}$: below 5 mole %.

An appropriate branch-chained quaternary ammonium salt can be exemplified, e.g., by a branch-chained dialkyl dimethyl ammonium chloride with the branch chain index of 10 to 50 mole % having an alkyl group and 8 to 16 carbon atoms.

The branch-chained quaternary ammonium salt represented by aforementioned general formula (5B) is normally synthesized by using Guerbet alcohol of formula $[R^{31}-CH_2CH_2CH(R^{32})CH_2OH]$ with 8 to 28 carbon atoms.

Most preferable among the branch-chained quaternary ammonium salts are the following: alkyl trimethoxy ammonium salt that contains an alkyl group derived from Guerbet alcohol having 8 to 28 atoms, a dialkyl dimethyl ammonium salt, dialkyl methyl hydroxyethyl ammonium salt, etc. Most preferable among the above are, e.g., 2-decyltetradecyl trimethyl ammonium chloride, 2-dodecylhexadecyl trimethyl ammonium chloride, di-2-hexyldecyl dimethyl ammonium chloride, di-2-octyldodecyl dimethyl ammonium chloride, etc.

The quaternary ammonium salts represented by aforementioned general formula (5C) are disclosed, e.g., in International Patent Application Publications WO 93/10748, WO 92/06899, WO 94/16677, and others. In particular, it is preferable that in aforementioned formula (5C), $R^{35}$ and $R^{36}$ are comprised of oleyl groups or alkyl groups with 12 to 18 carbon atoms, $R^{37}$ is comprised of a methyl group, $R^{38}$ is comprised of $-CH_2CH_2OH$, "k" and "m" are, preferably, 0.

Examples of preferable quaternary ammonium salts having alkenyl groups or alkyl groups cleaved by functional groups represented by $-OCO-$ or $-COO-$ are quaternary ammonium salts represented by general formula (5D) or (5E) and disclosed, e.g., in Kokai 2000-128740 and Kokai 2000-143458.

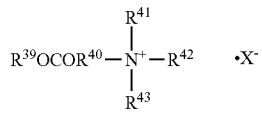

General formula (5D)

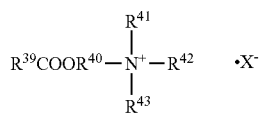

General formula (5E)

[In the above formulae, $R^{39}$ designates an alkenyl or alkyl group with 7 to 37 carbon atoms; $R^{40}$ designates an alkylene group with 1 to S carbon atoms. $R^{41}$, $R^{42}$, and $R^{43}$ are alkyl or hydroxyalkyl groups with 1 to 4 carbon atoms, respectively; $X^-$ has the same meaning as defined above.

In above formulae (5D) and (5E), $R^{39}$ may designate linear or branched alkenyl or alkyl groups with 7 to 21 carbon atoms, and preferably, 11 to 18 carbon atoms. $R^{40}$ may designate an ethylene group or n-propylene group. $R^{41}$, $R^{42}$, and $R^{43}$ may represent methyl, ethyl, hydroxyethyl, and hydroxypropyl groups. Specific examples of $X^-$ are $Cl^-$, $Br^-$, or other halogen ions, and alkyl sulfate ion with 1 to 5 carbon atoms ($CH_3SO_4^-$, $C_2H_5SO_4^-$, $C_3H_7SO^-$, etc.), alkyl carbonate ion ($CH_3CO_3^-$) etc., of which $Cl^-$, $Br^-$, $CH_3SO_4^-$, $C_2H_5SO_4$, and $CH_3CO_3^-$ are preferable.

Further preferable quaternary ammonium salts of general formula (5) are linear alkyl or alkenyl groups with 12 to 22 carbon atoms represented by $R^{21}$, mono-long chain alkyl quaternary ammonium salt having alkyl groups with 1 to 3 carbon atoms represented by $R^{22}$, $R^{23}$ and $R^{24}$, and a dialkyl quaternary ammonium salt represented by aforementioned general formula (5A) and having an alkyl group with 8 to 16 carbon atoms and the branch chain index within the range of 10 to 50 mole %. Most preferable are alkyl or alkenyl groups with 12 to 22 carbon atoms represented by $R^{21}$ and mono-long-chain alkyl quaternary ammonium salt having an alkyl groups with 1 to 3 carbon atoms represented by $R^{22}$, $R^{23}$ and $R^{24}$.

In the tertiary amine represented by aforementioned general formula (6), $R^{25}$ may represent linear or branched alkyl or alkenyl groups with 8 to 26 carbon atoms that can be OH-substituted or cleaved by functional groups of the following formulae: $-O-$, $-CONH-$, $-OCO-$, or $-COO-$; $R^{26}$ designates a hydroxyalkyl group, alkenyl group, or alkyl group with 1 to 5 carbon atoms; both $R^{26}$'s may be the same or different.

The following are specific examples of tertiary amines represented by aforementioned general formula (6): distearyl methylamine, dioleyl methylamine, dipalmitoylamine, stearyldimethylamine, stearyldiethylaamine, behenyldimethylamine, behenyldiethylamine, oleyldimethylamine, palmitoyldimethylamine, etc.

Compounds that are comprised of alkyl or alkenyl groups that contain 8 to 35 of total carbon atoms and can be cleaved by $-CONH-$ are represented by amidoamines of below-given general formula (6A).

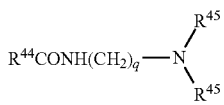

General formula (6A)

(where $R^{44}$ is an alkyl or alkenyl group with 16 to 22 carbon atoms, $R^{45}$'s are both alkyl groups with 1 to 3 carbon atoms, and "q" is a number between 1 and 3.)

The following are examples of amidoamines of general formula (6A): stearamidopropyl dimethylamine, stearamidopropyl diethylamine, stearamidoethyl diethylamine, stearamidoethyl dimethylamine, palmitoamidopropyl dimethylamine, palmitoamidopropyl diethylamine, palmitoamidoethyl dimethylamine, behenamidopropyl dimethylamine, behenamidopropyl diethylamine, behenamidoethyl diethylamine, behenamidoethyl dimethylamine, arachidamidopropyl dimethylamine, arachidamidopropyl diethylamine, arachidamidoethyl diethylamine, arachidamidoethyl dimethylamine, and mixtures of the aforementioned compounds. Most preferable are stearamidopropyl dimethylamine, stearamidoethyl diethylamine, and their mixtures.

Tertiary amines and amidoamines have different pH, but when they are used as salts, they have to be combined with organic and/or inorganic acids, such as phosphoric acid, hydrochloric acid, acetic acid, L-glutamic acid, lactic acid, malic acid, succinic acid, fumaric acid, tartaric acid, glycolic acid, and citric acid, or mixtures of the above. Most preferable are L-glutamic acid, lactic acid, and hydrochloric acid, or their mixtures.

It is also recommended that $R^{25}$ in aforementioned general formula (6) be represented by linear alkyl or alkylene groups with 12 to 22 carbon atoms, and each $R^{26}$ be represented by mono-long-chain alkyl tertiary amine having an alkyl group with 1 to 3 carbon atoms, and by amidoamine of formula (6A).

The composition of the invention may contain a cationic surface-agent (D) of one or more types.

In the composition, the cationic surface-active agent (D) (or the sum of these agents when they are added in more than one type) should be used in the amount of 0.001 to 20 mass % (per total weight of the composition as a reference), preferably in the amount of 0.005 to 15 mass %, even more preferably, 0.01 to 10 mass %, and still further preferably, 0.01 to 5 mass %, but the most preferable amount is 0.1 to 3 mass %. If the cationic surface-active agent (D) is added in the amount less than the lower recommended limit, it will not produce a sufficient synergistic effect, and the obtained composition for hair will not impart to hair a sufficient rinse effect. On the other hand, if the cationic surface-active agent (D) is used in an excessive amount, the obtained composition will become too viscous.

<Surface-Active Agent (E)>

The surface-active agent (E) that constitutes an optional component of the composition of the invention may be selected from one or more types of anionic surface-active agents, amphoteric surface-active agents, and nonionic surface-active agents.

Coexistence of agent (E) with other components of the composition produces an emulsification action and imparts to the composition an improved rinsing effect.

Anionic surface-active agents suitable for use as surface-active agent (E) may be exemplified by a fatty acid soap, α-acylsulfonic acid salt, alkylsulfonic salt, alkylaryl and alkylnaphthalenesulfonic acid salt, alkylsulfuric acid salt, polyoxyethylene alkylether sulfuric acid salt, alkylamidosulfuric acid salt, alkylphosphoric acid salt, alkylamidophosphoric acid salt, alkyloylalkyltaurine salt, N-long-chain-acylamino acid salt, polyoxyethylene alkylether carboxylic acid salt, α-sulfofatty acid salt, phosphoric acid alkyl($C_{12}$ to $C_{22}$) ester type surface-active agent or ethyleneoxide adducts thereof, sulfosuccinic acid type surface-active agent, amidoethylsulfate type surface-active agent, etc.

The following are examples of nonionic surface-active agents suitable for use as surface-active agent (E): polyoxyethylene alkylether, alkylaryl polyoxyethylene ether, alkylolamide, alkylglycerine ether type polyoxyethylene ether, polyoxyethylene ether of polypropyleneglycol ester, polyoxyethylene fatty acid ester, polyoxyethylene ether of glycerin and fatty acid ester, polyoxyethylene ether of fatty acid sorbitane ester, fatty acid ester of sorbitolpolyoxyethylene, cane sugar ester, polyoxyethylene fatty acid amide, polyoxyethylene alkylamine, alkyl polyglycoside compound, polyglycerol type compound, higher fatty acid alkanolamide, etc.

Amphoteric surface-active agents suitable for use as surface-active agent (E) can be of a betaine type (carboxybetaine, sulfobetaine), amidobetaine type, aminocarboxylic acid salt type, or an imidazoline type.

Normally, the composition of the invention should contain a surface-active agent (E) (or the sum of these agents when they are added in more than one type) in the amount of 0.01 to 40 mass % (per total weight of the composition as a reference), preferably in the amount of 0.1 to 30 mass %, and even more preferably, 1 to 25 mass %.

<Water-Soluble Polymer (F)>

The water-soluble polymer (F) that constitutes an optional component of the composition of the invention may be selected from one or more types of anionic water-soluble polymers, cationic water-soluble polymers, and amphoteric water-soluble polymers.

Coexistence of polymer (F) with other components of the composition improves the feel of use.

There are no special restrictions with regard to compounding of water-soluble polymer (F), and the latter can be compounded with conventional cosmetic or external application material.

Anionic water-soluble polymers suitable for use as polymer (F) may be exemplified by a xanthan gum, carrageenan, sodium alginate, gum arabic, pectin, carboxyvinyl polymer, etc.

Other examples include a hyaluronic acid, chondroitin sulfate, dermatan sulfate, keratan sulfate, heparan sulfate, or salts of the above.

Cationic water-soluble polymers suitable for use as polymer (F) may be exemplified, e.g., by cation-modified cellulose ether derivatives (polymer JR (U.C.C.), or the like), cationic starch, cationic guar gum, diallyldimethyl ammonium chloride type polymer (Merquat (Merck), etc.), polyacrylic acid derivative type quaternary ammonium (Cartex (National Starch), etc.), polyamide derivative type quaternary ammonium (Sandoz, etc.), polyoxyethylene polyalkylene polyamine (Polycoat (Henkel) etc.

Amphoteric water-soluble polymers suitable for use as polymer (F) may be exemplified, e.g., by copolymers of monomers with anionic groups such as carboxylic groups, sulfonic groups, etc. and monomers with basic nitrogen atoms; polymers or copolymers of carboxybetainic type monomers; as well as compounds where anionic groups such as carboxy groups or sulfonic groups are introduced into cationic polymers or where basic nitrogen-containing groups are introduced into anionic polymers, e.g., copolymers of monomers with acrylamide groups or similar non-ionic groups and monomers with basic nitrogen-containing groups.

Commercially produced amphoteric water-soluble polymers suitable for the composition may be exemplified by MERQUAT Plus 3330 (the product of CALGON Co.) that comprises a copolymer of an acrylic acid, diallyl quaternary ammonium salt, and acrylamide. The non-ionic water-soluble polymers can be represented by hydroxyethyl cellulose, hydroxypropyl cellulose, hydroxypropyl methyl cellulose, methyl cellulose, dextrin, galactan, pullulan, etc.

Most preferable of the above are cationic water-soluble polymers and amphoteric water-soluble polymers. If the aforementioned polymer is added in the amount not detrimental to the purposes of the present invention (i.e., is not flying away and do not make the hair starchy), it can contribute to the effects of the invention by imparting to hair smoothness during detergent washing.

<Liquid Cyclic Silicone (G)>

The liquid cyclic silicone (G) that constitutes an optional component of the composition is used as a solvent for dissolving block copolymer (A) which is an indispensable component. The effect of the liquid cyclic silicone (G) consists in that, by uniformly dissolving block copolymer (A) in liquid cyclic silicone (G,) it becomes possible to provide a more uniform distribution thereof during application. Furthermore, addition of liquid cyclic silicone (G) to the composition of the invention imparts to hair an emollient sensation.

Specific examples of liquid cyclic silicone (G) are common compounds that are known as octamethylcyclotetrasiloxane, decamethylcyclopentasiloxane, and tetradecamethylcyclohexasiloxane.

<Liquid Chain-Type Silicone (H)>

The liquid chain-type silicone (H) that constitutes an optional component of the composition is used as a solvent for dissolving block copolymer (A) which is an indispensable component. The effect of the liquid cyclic silicone (H) consists in that by uniformly dissolving block copolymer (A) in liquid cyclic silicone (G), it becomes possible to provide a more uniform distribution thereof during application. Furthermore, addition of liquid cyclic silicone (G) to the composition of the invention imparts to hair an emollient sensation.

An example of liquid chain-type silicone (H) is a dimethylpolysiloxane (viscosity 0.65 to 10 cSt/25° C.).

<Liquid Isoparaffin-Type Hydrocarbon (I)>

The liquid isoparaffin-type hydrocarbon (I) that constitutes an optional component of the composition is used as a solvent for dissolving block copolymer (A) which is an indispensable component. The effect of the liquid isoparaffin-type hydrocarbon (I) consists in that by uniformly dissolving block copolymer (A) in liquid isoparaffin-type hydrocarbon (I), it becomes possible to provide a more uniform distribution thereof during application. Furthermore, addition of liquid isoparaffin-type hydrocarbon (I) to the composition of the invention imparts to hair an emollient sensation.

An example of liquid isoparaffin-type hydrocarbon (I) is a paraffin-type hydrocarbon that at a normal pressure has a boiling point within the range of 60 to 350° C. This can be, e.g., Isopar Type A (registered trade mark of Exxon Co.), as well as types C, D, E, G, H, K, L, M of the same tradename, Shellsol 71 (trademark of Shell Co.), Solutol type 100 (registered trademark of Philip Co.), types 130 and 220 of the same trademark, Parleam 4 (registered trademark of Nippon Oils and Fats Co., Ltd.), type EX and 6 of the same trademark, etc.

<Liquid or Solid Ester Oil (J)>

The liquid or solid ester oil (J) that constitutes an optional component of the composition is used as a solvent for dissolving block copolymer (A) which is an indispensable component. The effect of the liquid or solid ester oil (J) consists in that by uniformly dissolving block copolymer (A) in liquid or solid ester oil (J), it becomes possible to provide a more uniform distribution thereof during application. Furthermore, addition of liquid or hard ester oil (J) to the composition of the invention imparts to hair an emollient sensation.

The following are examples of the liquid or solid ester oils (J): isopropyl myristate, isopropyl palmitate, cetyl 2-ethylhexanoate, isocetyl 2-ethylhexanoate, glycerin tri-2-ethylhaxanoate, trimethylolpropane tri-2-ethylhexanoate, caprylic-capric triglyceride, glycerin triisostearate, 2-ethylhexyl hydroxystearate, pentaerythritol tetra-2-ethylhexanoate, neopentyl glycol dicaprylate, octyldodecyl myristate, octyl palmitate, isooctyl palmitate, octyl stearate, isooctyl stearate, butyl stearate, myristyl myristate, stearyl stearate, isononyl isononanoate, isodecyl isonanoate, isotridecyl isonanoate, 2-ethylhexyl isonanoate, isopropyl isostearate, 2-hexyldecyl isostrearate, propyleneglycol isostearate, polyethyleneglycol isostearate, polyethyleneglycol diisostearate, pentaerythritol tetraisostearate, octyl isopalmitate, isocetyl pivalate, octyldodecyl pivalate, octyldodecyl lactate, isobutyl adipate, 2-ethylhexylsuccinate, neopentylglycol di-2-ethylhexanoate, polyglyceryl diisostearate, polyglyceryl tetraisostearate, hexyl laurate, diisopropyl dimerate, etc.

<Compounded Quantities of Solvent Components>

In the preparation of the composition of the invention, block copolymer (A) can be preliminarily dissolved in the aforementioned solvent component (such as a liquid cyclic silicone (G), liquid chain-type silicone (H), liquid isoparaffin type hydrocarbon (I), liquid or solid ester oil (J)) to form a liquid (or solid) solution. If necessary, however, the block copolymer (A) and the solvent can be added to the system separately. The solvent components can be of one or more types. The total amount of the solvent can be selected as 0.1 to 50 times (mass) per quantity (mass) of block copolymer (A), or 0.01 to 80 mass % per total mass of the composition for hair. When it is used as a detergent, the added amount should be within 20 mass %. If the solvent component is added in an amount below 0.1 times (mass), the dissolving or diluting effect of the solvent will be insufficient. If, on the other hand, the solvent component is added in an amount exceeding 50 times (mass), the concentration of block copolymer (A) will be too low, so that the composition will have an insufficient hair-treatment effect.

<Emulsifier>

As mentioned above, in the preparation of the composition of the invention by compounding block copolymer (A), it is preferable to prepare the composition in the form of a solution obtained by dissolving the block copolymer (A) in the aforementioned solvent component. Properties and effects of the obtained composition for hair can be further improved by additionally compounding the prepared liquid (or solid) solution of block copolymer (A) with an emulsifier. Addition of the emulsifier will improve uniformity of the solution and uniformity in dissolving other additives.

The following are examples of emulsifiers, other than those used as surface-active agents (E): polyoxyethylenealkyl ether, polyoxyethylenealkylphenyl ether, polyoxyethylenecholesteryl ether, polyoxyethylenesorbitan fatty acid ester, polyoxyethyleneglyceryl fatty acid ester, polyoxyethylene hydrogenated castor oil, polyethyleneglycol fatty acid ester, polyglycerin fatty acid ester, cane sugar fatty acid ester, polyether-modified silicone, or similar nonionic active agents, stearyl trimethyl ammonium chloride, stearyl dimethyl ammonium chloride, cetyl trimethyl ammonium chloride, behenyl trimethyl ammonium chloride, cetylpyridinium chloride, or similar cationic active agents, sodium cetyl sulfate, sodium polyoxyethylene lauryl ether sulfate, sodium lauryl sulfate, potassium cocoate, sodium cocoate methyltaulin, or similar anionic active agent.

<Water-Soluble Polyhydric Alcohol (K)>

Properties and storage stability of the composition of the invention can be further improved if, in compounding and emulsifying the solution of block copolymer (A) with the emulsifier, the composition is further combined with a water-soluble polyhydric alcohol.

The aforementioned water-soluble polyhydric alcohol can be represented by ethyleneglycol, propyleneglycol, 1,3-butyleneglycol, 1,4-butyleneglycol, dipropyleneglycol, glycerin, diglycerin, triglycerin, tetraglycerin, glucose, maltose, maltitol, cane sugar, fructose, xylitol, sorbitol, maltotriose, threitol, erythritol, starch, decomposed sugar reducing alcohol, hyaluronic acid, etc. The composition may incorporate one or more types of these alcohols.

<Other Additives>

In addition to the components described above, the composition of the invention may be compounded with other optional components, provided that they are added in the amounts and within the qualitative limits not conflicting with the object of the present invention. Such other additives may comprise liquid paraffin, squarane, lanolin derivatives, higher alcohols, avocado oil, palm oil, tallow, jojoba oil, silicone oil, polyalkyleneglycol polyether, and their carboxylic acid oligoester compounds, terpene-type hydrocarbon oil, or similar oil fractions, ethyleneglycol, propyleneglycol, 1,3-butyleneglycol, glycerin, sorbitol, polyethyleneglycol, or similar water-soluble polyhydric alcohols, hyaluronic acid, chondroitin sulfuric acid, pyrrolidone-carboxylic acid salt, or similar moisturizer, ultraviolet ray absorber, ultraviolet ray disperser, acrylic resin, silicone resin, polyvinyl pyrrolidone, or similar resins, soybean protein, gelatin, collagen, silk fibroin, elastin, or similar proteins or products of protein decomposition, ethylparaben, butylparaben, or similar antiseptics, various amino acids, biotin, pantothenic acid derivatives, or similar promoters, γ-olizanol, sodium dextrasulfate, vitamin E derivatives, nicotinic acid derivatives, or similar blood flow improving agents, sulfur, thiantol, or other antiseborrhea agents, ethanol, isopropanol, tetrachlorodifluoroethane, or similar diluents, carboxyvinyl polymer, or similar thickeners, pharmaceutical substances, deodorants, coloring agents, etc.

<Hair Cosmetics>

The composition of the invention can be compounded with various cosmetic materials suitable for hair, such as preshampoos, hair rinses, hair conditioners, hair treatments, set lotions, blow styling lotions, hair sprays, styling foams, styling gels, hair liquids, hair tonics, hair creams, temporary hair dyes, etc. The composition of the invention can be arbitrarily used in various systems such as solutions, emulsions, dispersed powders, two layer systems such as oil-water, three-layer systems such as oil-water-powder, etc. In case of emulsion, an oil phase that contains block copolymer (A) can be emulsified with the use of an emulsification agent, such as, e.g., a nonionic surface-active agent, cationic surface-active agent, anionic surface-active agent, or a mixture of the above. Furthermore, in case of emulsification, the emulsification agent can be dissolved in a water-soluble polyhydric alcohol, and the emulsified composition can be prepared by adding an oil fraction that contains block copolymer (A) and then emulsifying the mixture. The emulsion can be prepared by diluting the obtained emulsified composition with water.

EXAMPLES OF PREFERRED EMBODIMENTS OF THE INVENTION

The invention will be further described with reference to practical examples, which, however, should not be construed as limiting the present invention.

The following block copolymers (A-1) to (A-4) were used in the subsequent practical examples as the aforementioned block copolymer (A).

[Block Copolymer (A-1)]

This block copolymer is represented by aforementioned general formula (1):
[where $R^1$ is a methyl group;
$Y^1$ is a group of formula: —$CH_2CH(CH_3)CH_2$—;
$R^2$ is a group of formula: —$CH_2CH(CH_3)CH_2$—O—$(C_2H_4O)_{14}$—$CH_2C(CH_3)$=$CH_2$
"a" is 199;
"b1" is 14;
"b2" is 0;
"c" is 13;
the average molecular weight of the polyorganosiloxane block is 14,900; the polyorganosiloxane block constitutes 95.7 mass % of block copolymer (A-1);
the average molecular weight of the polyoxyalkylene block is 610; and the average molecular weight of block copolymer (A-1) is 218,000.]

[Block Copolymer (A-2)]

This block copolymer is represented by aforementioned general formula (1):
[where $R^1$ is a methyl group;
$Y^1$ is a group of formula: —$CH_2CH(CH_3)CH_2$—;
$R^2$ is a group of formula:

—$CH_2CH(CH_3)CH_2$—O—$(C_2H_4O)_{23}$—$(C_3H_6O)_6$—
$CH_2C(CH_3)$=$CH_2$;

"a" is 160;
"b1" is 23;
"b2" is 6;
"c" is 7;
the average molecular weight of the polyorganosiloxane block is 12,000;
the polyorganosiloxane block constitutes 88.7 mass % of block copolymer (A-2); the average molecular weight of the polyoxyalkylene block is 1,360; and
the average molecular weight of block copolymer (A-2) is 109,000.]

[Block Copolymer (A-3)]

This block copolymer is represented by aforementioned general formula (1):
[where $R^1$ is a methyl group;
$Y^1$ is a group of formula: —$CH_2CH(CH_3)CH_2$—;
$R^2$ is a group of formula:

—$CH_2CH(CH_3)CH_2$—O—$(C_2H_4O)_{20}$—$(C_3H_6O)_{35}$—
$CH_2C(CH_3)$=$CH_2$;

"a" is 141;
"b1" is 20;
"b2" is 35;
"c" is 24;
the average molecular weight of the polyorganosiloxane block is 10,600;
the polyorganosiloxane block constitutes 77.8 mass % of block copolymer (A-3); the average molecular weight of the polyoxyalkylene block is 2,900; and
the average molecular weight of block copolymer (A-3) is 343,000.]

[Block Copolymer (A-4)]

This block copolymer is represented by aforementioned general formula (1):
[where $R^1$ is a methyl group;
$Y^1$ is a group of formula: —$CH_2CH(CH_3)CH_2$—;
$R^2$ is a group of formula:

—$CH_2CH(CH_3)CH_2$—O—$(C_2H_4O)_{46}$—$(C_3H_6O)_{15}$—
$CH_2C(CH_3)$=$CH_2$;

"a" is 385;
"b1" is 46;
"b2" is 15;
"c" is 29;
the average molecular weight of the polyorganosiloxane block is 28,500; the polyorganosiloxane block constitutes 90.7 mass % of block copolymer (A-4); the average molecular weight of the polyoxyalkylene block is 2,900; and the average molecular weight of block copolymer (A4) is 949,000.]

For the sake of comparison, block copolymer (B) was used in the form of below-given block copolymer (B-1). Furthermore, block copolymer (B) in the form of block copolymer (B-2) was used in combination with block copolymer (A).

[Block Copolymer (B-1)]

This block copolymer is represented by aforementioned general formula (2):
[where $R^3$ is a methyl group;
$Y^3$ is a group of formula: —$CH_2CH(CH_3)CH_2$—;
$R^4$ is a group of formula:

—$CH_2CH(CH_3)CH_2$—O—$(C_2H_4O)_{23}$—$(C_3H_6O)_6$—
$CH_2C(CH_3)$=$CH_2$;

"a'" is 40;
"b3" is 23;
"b4" is 6;
"c'" is 1;
the average molecular weight of the polyorganosiloxane block is 3,100;
the polyorganosiloxane block constitutes 58.1 mass % of block copolymer (B-1); the average molecular weight of the polyoxyalkylene block is 1,360; and
the average molecular weight of block copolymer (B-1) is 10,700].

[Block Copolymer (B-2)]

This block copolymer is represented by aforementioned general formula (2):
[wherein "a'" is 25, "c'" is 0;
among 52 groups designated by $R^3$, 49 groups are methyl groups and 3 groups are those expressed by formula:

—$(CH_2)_3$—O—$(C_2H_4O)_{20}(C_3H_6O)_{15}$—$C_4H_9$;

$R^4$ is a methyl group;
the average molecular weight of the polyorganosiloxane block is 2,000;
the polyorganosiloxane block constitutes 26.0 mass % of the block copolymer (B-2); the average molecular weight of the polyoxyalkylene block is 1,900; and
the average molecular weight of block copolymer (B-2) is 7,700]

[Reactive Block Copolymer (a-1)]

For the sake of comparison, the block copolymer was used in the form of a reactive block copolymer (a-1) represented by the following formula:

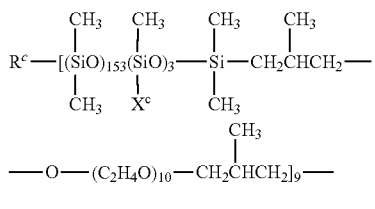

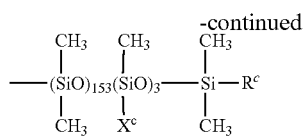

(wherein $R^c$ is a group of formula:

$$-CH_2CH(CH_3)CH_2-O-(C_2H_4O)_{10}-CH_2C(CH_3)=CH_2;$$

and $X^c$ is a group of formula: $-(CH_2)_3-NH-(CH_2)_2-NH_2$].

Furthermore, block copolymer (C) that was combined with block copolymer (A) was used in the form of below-given reactive silicone (C-1), and for the sake of comparison, block copolymer (C) was used in the form of below-given reactive silicone (C-2).

[Reactive Silicone (C-1)]

The silicone compound was represented by aforementioned general formula (3) [where $R^8$, $R^9$, and $R^{10}$ designate methyl groups, and $X^1$ is a group of formula:

$$-(CH_2)_3-NH-(CH_2)_2-NH_2;$$

"q" is 300, and "r" is 1.]

[Reactive Silicone (C-2)]

The silicone compound was represented by aforementioned general formula (3) [wherein $R^8$ is a hydroxyl group, $R^9$ and $R^{10}$ designate methyl groups, and $X^1$ is a group of formula: $-(CH_2)_3-NH-(CH_2)_2-NH_2$; "q" is 3000, and "r" is 6.]

Practical Examples 1 to 24 and Comparative Examples 1 to 6

Shampoo compositions were prepared by a conventional method with proportions of components shown in following Tables 1 to 5 (in mass % units).

TABLE 1

| | Practical Examples | | | | | |
|---|---|---|---|---|---|---|
| | 1 | 2 | 3 | 4 | 5 | 6 |
| Sodium dodecyl sulfate | 20 | 20 | 20 | 20 | 20 | 20 |
| Block copolymer (A-1) | 0.05 | 0.10 | 0.50 | 1.00 | 0.50 | 0.50 |
| Block copolymer (B-2) | — | — | — | — | 0.05 | — |
| Reactive silicone (C-1) | — | — | — | — | — | 0.05 |
| Dimethylpolysiloxane (5 cs) | 0.075 | 0.15 | 0.75 | 1.50 | 0.75 | 0.75 |
| Water | Balance | Balance | Balance | Balance | Balance | Balance |

TABLE 2

| | Practical Examples | | | | | |
|---|---|---|---|---|---|---|
| | 7 | 8 | 9 | 10 | 11 | 12 |
| Sodium dodecyl sulfate | 20 | 20 | 20 | 20 | 20 | 20 |
| Block copolymer (A-2) | 0.05 | 0.10 | 0.50 | 1.00 | 0.50 | 0.50 |
| Block copolymer (B-2) | — | — | — | — | 0.05 | — |
| Reactive silicone (C-1) | — | — | — | — | — | 0.05 |
| Dimethylpolysiloxane (5 cs) | 0.075 | 0.15 | 0.75 | 1.50 | 0.75 | 0.75 |
| Water | Balance | Balance | Balance | Balance | Balance | Balance |

TABLE 3

| | Practical Examples | | | | | |
|---|---|---|---|---|---|---|
| | 13 | 14 | 15 | 16 | 17 | 18 |
| Sodium dodecyl sulfate | 20 | 20 | 20 | 20 | 20 | 20 |
| Block copolymer (A-3) | 0.05 | 0.10 | 0.50 | 1.00 | 0.50 | 0.50 |
| Block copolymer (B-2) | — | — | — | — | 0.05 | — |
| Reactive silicone (C-1) | — | — | — | — | — | 0.05 |
| Dimethylpolysiloxane (5 cs) | 0.075 | 0.15 | 0.75 | 1.50 | 0.75 | 0.75 |
| Water | Balance | Balance | Balance | Balance | Balance | Balance |

TABLE 4

| | Practical Examples | | | | | |
|---|---|---|---|---|---|---|
| | 19 | 20 | 21 | 22 | 23 | 24 |
| Sodium dodecyl sulfate | 20 | 20 | 20 | 20 | 20 | 20 |
| Block copolymer (A-4) | 0.05 | 0.10 | 0.50 | 1.00 | 0.50 | 0.50 |
| Block copolymer (B-2) | — | — | — | — | 0.05 | — |
| Reactive silicone (C-1) | — | — | — | — | — | 0.05 |
| Dimethylpolysiloxane (5 cs) | 0.075 | 0.15 | 0.75 | 1.50 | 0.75 | 0.75 |
| Water | Balance | Balance | Balance | Balance | Balance | Balance |

TABLE 5

| | Comparative Examples | | | | | |
|---|---|---|---|---|---|---|
| | 1 | 2 | 3 | 4 | 5 | 6 |
| Sodium dodecyl sulfate | 20 | 20 | 20 | 20 | 20 | 20 |
| Block copolymer (B-1) | 0.5 | — | — | — | — | — |
| Reactive block copolymer (a-1) | — | 0.5 | — | — | — | — |

TABLE 5-continued

| | Comparative Examples | | | | | |
|---|---|---|---|---|---|---|
| | 1 | 2 | 3 | 4 | 5 | 6 |
| Polydimethyl-siloxane gum (molecular weight = 2,000,000) | — | — | 0.5 | — | — | — |
| Reactive silicone (C-1) | — | — | — | — | 0.5 | — |
| Reactive silicone (C-2) | — | — | — | — | — | 0.5 |
| Dimethylpoly-siloxane (5 cs) | 0.75 | 0.75 | 0.75 | 3.0 | 0.15 | 0.75 |
| Water | Balance | Balance | Balance | Balance | Balance | Balance |

All shampoo compositions of aforementioned Practical Examples 1 to 24 and Comparative Examples 1 to 6 were evaluated with regard to foamability and washability.

Furthermore, all obtained shampoo compositions were used and evaluated (functional evaluation by the testers) with regard to smoothness of hair after washing and duration of this property, ease of combing after hair wash and duration of this property, moist feeling after washing and drying and duration of this property, thick-film touch after washing and drying and duration of this property, unfavorable feel of touch during washing (or in a wet state) of hair, unfavorable feel of touch after washing and drying, tackiness of hair after washing and drying.

The results of evaluation are shown in Tables 6 to 8 given below. More detailed description of the evaluation procedures and evaluation criteria are described below.

(1) Foamability:

400 ml of solution with 1 mass % concentration of the test material was prepared with the use of artificially-hardened water having 70 ppm concentration of $CaCO_3$, and then the foaming amount was measured by using a cylinder equipped with a stirrer. The following evaluation criteria were used in this test:

[○]: good bubbling
[Δ]: normal bubbling
[X]: poor bubbling (2) Washability

A solution with 1 mass % concentration of the test material was prepared with the use of artificially-hardened water (CaO/MgO=3/1.5 degrees of water hardness), and a dyed artificially soiled wool serge cloth was washed. Washing was carried out in a tergotometer (JIS K-3371) at 40° C., washing efficiency was determined by means of the formula given below, and then evaluation was carried out on the basis of the following criteria:

Washing Efficiency (%)=$[(R_w-R_s)/(R_0-R_s)]\times 100$, where:
$R_0$ is the reflection coefficient of the original cloth (wool serge);
$R_s$ is the reflection coefficient of the soiled cloth;
$R_w$ is the reflection coefficient of the soiled cloth after washing;

[○]: reflection coefficient is equal to or greater than 80% (good washability);
[Δ]: reflection coefficient is equal to or greater than 60% and below 80% (normal washability);
[X]: reflection coefficient is below 60% (poor washability).

(3) Smoothness of the Hair

The testers actually washed their hair and made functional evaluation of hair smoothness after washing and drying with the use of a dryer. The following criteria were used for evaluation:

[○]: sufficient feel of smoothness;
[Δ]: some feel of smoothness;
[X]: no feel of smoothness.

(4) Duration of the Feel of Smoothness after Washing

Smoothness of the hair was evaluated by the same functional evaluation method as described in Item (3) but after the evaluators combed their hair 50 times with a brush.

(5) Ease of Combing after Washing

Evaluators actually washed their hair and made functional evaluation of ease to comb after washing and drying the hair with a dryer. The following criteria were used for evaluation:

[○]: Easy to comb;
[Δ]: rather easy to comb;
[X]: not easy to comb.

(6) Duration of Ease of Combing

This property was evaluated by the same functional evaluation method as described in Item (5) but after the evaluators brushed their hair 50 times.

(7) Moist Feeling after Washing and Drying the Hair

Evaluators actually washed their hair and made functional evaluation of the moist feeling after drying the hair with a dryer. The following criteria were used for evaluation:

[○]: Sufficient moist feeling;
[Δ]: Some moist feeling;
[X]: No moist feeling.

(8) Duration of Moist Feeling after Washing and Drying the Hair

This property was evaluated by the same functional evaluation method as described in Item (7) but after the evaluators brushed their hair 50 times.

(9) Thick-Film Touch after Washing and Drying

Evaluators actually washed their hair and made functional evaluation of the thick-film touch after drying the hair with a dryer. The following criteria were used for evaluation:

[○]: Sufficient thick-film touch;
[Δ]: Some thick-film touch
[X]: No thick-film touch.

(10) Duration of Thick-Film Touch after Washing and Drying

This property was evaluated by the same functional evaluation method as described in Item (9) but after the evaluators brushed their hair 50 times.

(11) Unfavorable Touch during Hair Washing

Evaluators actually washed their hair and made functional evaluation of the unfavorable touch during hair washing. The following criteria were used for evaluation:

[○]: No unfavorable touch;
[Δ]: Some unfavorable touch
[X]: Noticeable unfavorable touch.

(12) Unfavorable Touch after Washing-Drying and after Drying

Evaluators actually washed their hair and made functional evaluation of the unfavorable touch after drying the hair with a dryer, the evaluation being based on the same criteria as in Item (11).

(13) Tackiness of Hair after Washing and Drying

Evaluators actually washed their hair and made functional evaluation of hair tackiness after drying the hair with a dryer. The following criteria were used:

[○]: No tackiness sensed;
[Δ]: Some tackiness sensed
[X]: Hair is very tacky.

TABLE 6

| Criteria/Evaluation Time | | Practical Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Foamability | | ○ | ○ | ○ | ○ | ○ | ○ | ○ | ○ | ○ | ○ | ○ | ○ |
| Washability | | ○ | ○ | ○ | ○ | ○ | ○ | ○ | ○ | ○ | ○ | ○ | ○ |
| Smoothness | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Ease of combing | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Moist feeling | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Thick-film touch | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Unfavorable touch | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| Tackiness | after drying | ○ | ○ | ○ | ○ | ○ | ○ | ○ | ○ | ○ | ○ | ○ | ○ |

TABLE 7

| Criteria/Evaluation Time | | Practical Examples | | | | | | | | | | | |
|---|---|---|---|---|---|---|---|---|---|---|---|---|---|
| | | 13 | 14 | 15 | 16 | 17 | 18 | 19 | 20 | 21 | 22 | 23 | 24 |
| Foamability | | ○ | ○ | ○ | ○ | ○ | ○ | ○ | ○ | ○ | ○ | ○ | ○ |
| Washability | | ○ | ○ | ○ | ○ | ○ | ○ | ○ | ○ | ○ | ○ | ○ | ○ |
| Smoothness | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Ease of combing | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Moist feeling | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Thick-film touch | after drying | ○ | ○ | ○ | ○ | ○ | ○ | ○ | ○ | ○ | ○ | ○ | ○ |
| | after brushing | ○ | ○ | ○ | ○ | ○ | ○ | ○ | ○ | ○ | ○ | ○ | ○ |
| Unfavorable touch | after washing | ○ | ○ | ○ | ○ | ○ | ○ | ○ | ○ | ○ | ○ | ○ | ○ |
| | after drying | ○ | ○ | ○ | ○ | ○ | ○ | ○ | ○ | ○ | ○ | ○ | ○ |
| Tackiness | after drying | ○ | ○ | ○ | ○ | ○ | ○ | ○ | ○ | ○ | ○ | ○ | ○ |

TABLE 8

| Criteria/Evaluation Time | | Comparative Examples | | | | | |
|---|---|---|---|---|---|---|---|
| | | 1 | 2 | 3 | 4 | 5 | 6 |
| Foamability | | ○ | ○ | Δ | ○ | Δ | Δ |
| Washability | | ○ | ○ | Δ | ○ | ○ | Δ |
| Smoothness | after washing | ○ | ○ | ○ | X | Δ | ○ |
| | after drying | Δ | ○ | ○ | X | ○ | ○ |
| | after brushing | X | ○ | X | X | X | Δ |
| Ease of combing | after washing | ○ | ○ | ○ | X | Δ | ○ |
| | after drying | Δ | ○ | ○ | X | ○ | ○ |
| | after brushing | X | ○ | X | X | X | Δ |
| Moist feeling | after drying | ○ | ○ | X | X | X | X |
| | after brushing | Δ | ○ | X | X | X | X |
| Thick-film touch | after drying | X | X | X | X | X | X |
| | after brushing | X | X | X | X | X | X |
| Unfavorable touch | after washing | ○ | X | X | X | X | X |
| | after drying | Δ | Δ | X | X | X | X |
| Tackiness | after drying | X | ○ | ○ | ○ | Δ | ○ |

As follows from the results shown in Tables 6 and 7, the compositions of the invention (the shampoo compositions used in Practical Examples 1 to 24) impart to the hair smoothness, ease of combing, moist feeling, and thick-film touch. These properties are not lost even after multiple brushing.

Unfavorable touch did not appear in the hair either in a moist state after washing, or in a dry state.

The hair does not become sticky after washing and drying.

The composition of the invention (the shampoo composition) is characterized by superb foamability and washability.

As can be seen from the results of Table 8, the shampoo composition of Comparative Example 1 that contains block copolymer (B-1) cannot impart to the washed and dried hair sufficient smoothness and ease of combing. Moreover, these properties are impaired by brushing. Furthermore, the composition of the aforementioned comparative example cannot impart to the hair the feel of thick-film touch but rather produces the unpleasant touch after the hair is dried.

The results of Table 8 also shows that the shampoo composition of Comparative Example 2 causes unfavorable touch during washing of the hair and cannot produce the feel of thick-film touch.

As follows from the same Table 8, the shampoo composition of Comparative Example 3 cannot maintain smoothness after washing and ease of combing imparted to the hair over a long time. This shampoo composition could not impart to the treated hair the moist feeling and thick-film touch. In both dried and moist state, the hair treated with the aforementioned shampoo acquired the unpleasant touch.

Practical Examples 25 to 27

Shampoo compositions were prepared by a conventional method with proportions of components shown in Table 9 (in terms of mass %).

TABLE 9

|  | Pr. Ex. 25 | Pr. Ex. 26 | Pr. Ex. 27 |
|---|---|---|---|
| Sodium lauroylmethyltaurate (anionic surface-active agent) | 20 | — | — |
| Betaine N-lauryldimethylaminoacetate | — | 15 | — |
| Imidazolium betaine | — | — | 20 |
| Block copolymer (A-1) | 1 | 1 | 1 |
| Cyclic silicone pentamer | 2 | 2 | 2 |
| Water | balance | balance | balance |

The shampoo compositions of Practical Examples 25 to 27 imparted to the hair smoothness, ease of combing, moist feeling, and sensation of thick-film touch. These properties did not disappear even after repeated brushing. Furthermore, neither in a moist state during washing, nor in a dry state, the hair produced the feel of unpleasant touch.

The shampoo compositions of these practical examples demonstrated superb foamability and washability.

Practical Examples 28 and 29

Shampoo compositions were prepared by a conventional method with proportions of components shown in Table 10 (in terms of mass %).

TABLE 10

|  | Pr. Ex. 28 | Pr. Ex. 29 |
|---|---|---|
| Isozol 400 (a product of Nippon Petrochemicals Co., Ltd.; low-boiling-point isoparaffin-type hydrocarbon) | 4.0 | — |
| ICEH (Kokyu Alcohol Kogyo Co., Ltd.; ester-type hydrocarbon) | — | 1.0 |
| Block copolymer (A-1) | 0.5 | 1.0 |
| Sodium methyl cocoyl taurate | 8.0 | 8.0 |
| Cocoyl propylamide bentaine | 12.0 | 12.0 |
| Coconut fatty acid diethanolamide | 4.0 | 4.0 |
| Glycerin | 2.0 | 2.0 |
| Perfume | 0.3 | 0.3 |
| Water | Balance | balance |

The compositions of Practical Examples 28 and 29 imparted to the hair smoothness, ease of combing, moist feeling, and sensation of thick-film touch. These properties did not disappear even after repeated brushing. Furthermore, neither in a moist state during washing, nor in a dry state, the hair produced the feel of unpleasant touch.

The shampoo compositions of these practical examples demonstrated superb foamability and washability.

Practical Examples 30 to 33 and Comparative Examples 7 to 10

Hair rinse compositions were prepared by a conventional method with proportions of components shown in Table 11 (in terms of mass %). All obtained hair rinse compositions were estimated as shown in Items [1] and [2] below.

TABLE 11

|  | Practical Examples | | | | Comparative Examples | | | |
|---|---|---|---|---|---|---|---|---|
|  | 30 | 31 | 32 | 33 | 7 | 8 | 9 | 10 |
| Stearyl trimethyl ammonium chloride | 2.0 | 2.0 | 2.0 | 2.0 | 2.0 | 2.0 | 2.0 | 2.0 |
| Cetostearyl alcohol (C16/C18 = 7/3) | 3.0 | 3.0 | 3.0 | 3.0 | 3.0 | 3.0 | 3.0 | 3.0 |
| Block copolymer (A-1) | 2.0 | — | — | — | — | — | — | — |
| Block copolymer (A-2) | — | 2.0 | — | — | — | — | — | — |
| Block copolymer (A-3) | — | — | 2.0 | — | — | — | — | — |
| Block copolymer (A-4) | — | — | — | 2.0 | — | — | — | — |
| Block copolymer (B-1) | — | — | — | — | — | 2.0 | — | — |
| Reactive silicone (C-1) | — | — | — | — | — | — | 2.0 | — |
| Reactive silicone (C-2) | — | — | — | — | — | — | — | 2.0 |
| Dimethylpolysiloxane (5 cs) | 10.0 | 10.0 | 10.0 | 10.0 | 10.0 | 10.0 | 10.0 | 10.0 |
| Methylparaben | appropriate amounts | | | | | | | |
| Coloring and perfume additives | appropriate amounts | | | | | | | |
| Ion-exchange water | balance | | | | | | | |

Evaluation [1]:

The hair rinse composition was applied onto the evaluator's hair that had been washed with the below-given reference shampoo agent (pH=6.5), and the hair was then washed and dried. Following this, along with functional estimations of each shampoo composition by the evaluators in accordance with the aforementioned Items (3) to (13), the functional evaluation was conducted by the evaluators also with regard to softness of the hair during rinsing with the rinse composition with subsequent drying, evenness of the hair during rinsing with the rinse composition, and ease of hair setting.

The results of the aforementioned evaluation are shown in below-given Table 12. The information about new items of evaluation. Evaluation methods, and evaluation criteria are given below.

(14) Softness of the Hair during Washing

Functional evaluation of this property was carried out by using the following criteria:

[◯]: Softness is noticeably better than the one obtained with the use of the below-described reference rinse composition (pH=4.8);

[Δ]: Softness is slightly better than the one obtained with the use of the below-described reference rinse composition;

[X]: Softness is the same as obtained with the use of the below-described reference rinse composition.

(15) Evenness of the Hair during Washing and after Drying

Functional evaluation of this property was carried out by using the following criteria:

[◯]: Evenness is noticeably better than the one obtained with the use of the reference rinse composition;

[Δ]: Evenness is slightly better than the one obtained with the use of the reference rinse composition;

[X]: Evenness is the same obtained with the use of the reference rinse composition.

(16) Ease of Combing of the Hair after Drying

[○]: Much easier than after the use of the reference rinse composition;

[Δ]: Slightly easier than after the use of the reference rinse composition;

[X]: The same effect as after the use of the reference rinse composition.

(Composition of the Reference Shampoo)

62% of the 25% polyoxyethylene laurylether sodium sulfate solution (average added mole number of ethyleneoxide is 2.5)

2.3% of ethanolamide laurate;

0.1% of 2-sodium adetate;

0.5% of sodium benzoate;

0.8% of sodium chloride;

appropriate amount of 75% phosphoric acid;

appropriate amount of perfume;

appropriate amount of methylparaben;

balance—purified water (Composition of the Hair Rinse)

2% of stearyl trimethyl ammonium chloride;

3% of cetyl alcohol;

1% of propyleneglycol;

appropriate amount of citric acid;

appropriate amount of perfume;

appropriate amount of methylparaben;

balance—purified water

TABLE 12

| Evaluation [1] | | Practical Examples | | | | Comparative Examples | | | |
|---|---|---|---|---|---|---|---|---|---|
| Item | Time | 30 | 31 | 32 | 33 | 7 | 8 | 9 | 10 |
| Feel of Smoothness | after rinsing | ○ | ○ | ○ | ○ | Δ | ○ | Δ | ○ |
| | after drying | ○ | ○ | ○ | ○ | X | Δ | ○ | ○ |
| | after brushing | ○ | ○ | ○ | ○ | X | X | X | Δ |
| Ease of combing | after rinsing | ○ | ○ | ○ | ○ | Δ | ○ | Δ | ○ |
| | after drying | ○ | ○ | ○ | ○ | X | Δ | ○ | ○ |
| | after brushing | ○ | ○ | ○ | ○ | X | Δ | Δ | ○ |
| Moist feeling | after drying | ○ | ○ | ○ | ○ | X | ○ | X | X |
| | after brushing | ○ | ○ | ○ | ○ | X | Δ | X | X |
| Thick-film touch | after drying | ○ | ○ | ○ | ○ | X | X | X | X |
| | after brushing | ○ | ○ | ○ | ○ | X | X | X | X |
| Unfavorable touch | during rinsing | ○ | ○ | ○ | ○ | Δ | ○ | X | X |
| | after drying | ○ | ○ | ○ | ○ | X | Δ | X | X |
| Tackiness | after drying | ○ | ○ | ○ | ○ | Δ | X | Δ | ○ |
| Softness | during rinsing | ○ | ○ | ○ | ○ | X | Δ | Δ | Δ |
| Smoothness | during rinsing | ○ | ○ | ○ | ○ | X | Δ | Δ | ○ |
| | after drying | ○ | ○ | ○ | ○ | X | Δ | Δ | ○ |
| Ease of hair setting | after drying | ○ | ○ | ○ | ○ | X | ○ | Δ | Δ |

Evaluation [2]:

Directly after Evaluation [1], the hair was washed for the second time but with the use of the aforementioned reference shampoo agent. After washing, the hair was dried. Evaluation was carried out in the same manner as in Evaluation [1] (functional evaluation by evaluators). The results are shown in below-given Table 13.

TABLE 13

| Evaluation [2] (after repeated washing) | | Practical Examples | | | | Comparative Examples | | | |
|---|---|---|---|---|---|---|---|---|---|
| Item | Time | 30 | 31 | 32 | 33 | 7 | 8 | 9 | 10 |
| Feel of Smoothness | after rinsing with standard shampoo | ○ | ○ | ○ | ○ | X | Δ | Δ | ○ |
| | after drying | ○ | ○ | ○ | ○ | X | Δ | Δ | ○ |
| | after brushing | ○ | ○ | ○ | ○ | X | X | X | Δ |
| Ease of combing | after rinsing with standard shampoo | ○ | ○ | ○ | ○ | X | Δ | Δ | ○ |
| | after drying | ○ | ○ | ○ | ○ | X | X | Δ | ○ |
| | after brushing | ○ | ○ | ○ | ○ | X | X | X | Δ |
| Moist feeling | after drying | ○ | ○ | ○ | ○ | X | Δ | X | X |
| | after brushing | ○ | ○ | ○ | ○ | X | Δ | X | X |
| Thick-film touch | after drying | ○ | ○ | ○ | ○ | X | X | X | X |
| | after brushing | ○ | ○ | ○ | ○ | X | Δ | X | X |
| Unfavorable touch | during rinsing with standard shampoo | ○ | ○ | ○ | ○ | X | Δ | X | X |
| | after drying | ○ | ○ | ○ | ○ | X | Δ | X | X |
| Tackiness | after drying | ○ | ○ | ○ | ○ | Δ | X | Δ | ○ |
| Softness | during rinsing with standard shampoo | ○ | ○ | ○ | ○ | X | Δ | Δ | Δ |
| Smoothness | during rinsing with standard shampoo | ○ | ○ | ○ | ○ | X | Δ | Δ | ○ |
| | after drying | ○ | ○ | ○ | ○ | X | X | Δ | ○ |
| Ease of hair setting | after drying | ○ | ○ | ○ | ○ | X | Δ | X | Δ |

Practical Examples 34 to 37

Hair rinse compositions were prepared by a conventional method with proportions of components shown in Table 14 (in terms of mass %).

TABLE 14

| | Practical Examples | | | |
|---|---|---|---|---|
| | 34 | 35 | 36 | 37 |
| Stearyl trimethyl ammonium chloride | 1.0 | 0.8 | 0.5 | 2.0 |
| Distearyl dimethyl ammonium chloride | 0.5 | — | — | — |
| Cetostearyl alcohol (C16/C18 = 7/3) | 3.5 | 3.0 | 1.5 | 4.0 |
| Block copolymer (A-1) | 1.0 | 1.0 | 1.0 | 1.0 |
| Dimethylpolysiloxane (5 cs) | 10.0 | 10.0 | 5.0 | 20.0 |
| Methylparaben | appropriate amounts | | | |
| Coloring and perfume additives | appropriate amounts | | | |
| Ion-exchange water | balance | | | |

The hair rinse compositions of Practical Examples 34 to 37 imparted to the hair such properties as smoothness, ease of combing, moist feeling, and sensation of thick-film touch. These properties did not disappear even after repeated brushing. Furthermore, neither in a moist state during washing, nor in a dry state, the hair produced the feel of unpleasant touch.

After drying, the hair treated with these rinse compositions did not become tacky.

Furthermore, the aforementioned hair rinse compositions demonstrated superb hair-protective effect and effects of imparting to hair such properties as smoothness, absorption into hair, sustainability in hair gloss, and uniformity of coating.

The above-described effects of the hair rinse composition did not disappear even after hair wash.

Practical Example 38

A hair rinse composition was prepared by a conventional method with the following proportions of the components:

0.6 mass % of cetyl trimethyl ammonium chloride;
20 mass % of cetostearyl alcohol (C16/C18=6/4);
3.0 mass % of block copolymer (A-1);
15.0 mass % of cyclic dimethylsiloxane pentimer;
1.0 mass % of glycerol monosterarate;
0.5 mass % of stearyc acid;
5.0 mass % of glycerin;
5.0 mass % of propyleneglycol;
appropriate amount of Yellow Color #4 (pigment);
appropriate amount of perfume;
appropriate amount of methylparaben;
appropriate amount of EDTA-3Na (chelate agent);
balance—ion-exchange water.

The above-described hair rinse composition imparted to the hair smoothness, ease of combing, moist feeling, and sensation of thick-film touch. These properties did not disappear even after repeated brushing. Furthermore, neither in a moist state during washing, nor in a dry state, the hair produced the feel of unpleasant touch.

After drying, the hair treated with these rinse compositions did not become tacky.

Furthermore, the aforementioned hair rinse compositions demonstrated superb stability and imparted to the hair smoothness unattainable with conventional compositions of this type. In addition, the composition produced a hair protective effect.

Practical Example 39

A hair treatment cream was prepared by a conventional method with the following proportions of the components:
3.0 mass % of behenyl trimethyl ammonium chloride;
6.5 mass % of cetostearyl alcohol (C16/C18=7/3);
2.0 mass % of behenyl alcohol;
20.0 mass % of dimethylsiloxane 5 cs;
6.0 mass % of block copolymer (A-1);
2.0 mass % of 2-octyl dodecanol;
0.3 mass %: polyoxyethylene hard castor oil derivative (ethyleneoxide 60 mole adduct);
1.0 mass % of polyoxyethylene stearyl ether (ethyleneoxide 4 mole adduct);
0.5 mass % of soybean lecithin;
10 mass % of glycerin;
5 mass % of dipropylene glycol;
appropriate amount of Yellow Color #4 (pigment);
appropriate amount of perfume;
appropriate amount of methylparaben;
appropriate amount of EDTA-3Na (chelate agent);
balance—ion-exchange water.

The above-described hair treatment cream imparted to hair, especially to damaged hair, superb smoothness and sensation of thick-film touch, moist feeling that suppressed dryness, and produced a high hair-protective effect.

Practical Example 40

A liquid hair oil of high transparency and viscosity (500 cps) was prepared by stirring and mixing at 70 to 80° C. the following components: (1) 70 parts by mass of light liquid isoparaffin (C11-13); (2) 20 parts by mass of dimethylpolysiloxane (5 cSt/25° C.); (3) 10.0 parts by mass of block copolymer (A-1); and (4) an appropriate amount of a perfume.

The obtained hair oil was applied onto locks of hair, and a coefficient of friction of hair was measured after application of the oil. The measurements showed that application of the hair oil significantly reduced the coefficient of friction of the hair. Following this, the hair locks treated with the hair oil were washed twice. Measurement of the coefficient of friction after sufficient washing did not show a noticeable difference from the coefficients of friction measured prior to the washing. Thus it can be assumed that the hair oil of Practical Example 40 can impart to hair sufficient smoothness. This property did not disappear even after the hair was shampooed.

Brushing of the oil-treated hair locks 10,000 times produced only an insignificant number of split hairs (only 10% or less of those not treated with the oil). Furthermore, the obtained hair oil demonstrated a superb repair effect for split hair.

Practical Example 41

A solution was prepared by dissolving 3.0 parts by mass of block copolymer (A-1) in 22.0 parts by mass of a light liquid paraffin (C12-15). The obtained solution was combined and emulsified with 6.0 parts by mass of propyleneglycol and 2.0 parts by mass of a polyoxyethylene hydrogenated castor oil (80 moles of polyoxyethylene). A basic component [of the target composition] was prepared by combining and mixing the obtained system with 0.2 parts by mass of a cationic cellulose polymer JR-400 (the product of UCC Co.), 10.0 parts by mass of a water-soluble Elastin, and 46.8 parts by mass of ion-exchange water. The obtained basic component was then loaded into an aerosol container and formed into an aerosol-type hair damage prevention and repair agent by adding 10 parts by mass of a spray agent component (dimethylether/diclorodifluoromethane (40 parts by mass/60 parts by mass)).

The obtained hair damage prevention and repair agent was applied onto hair locks, and then coefficients of friction of the treated hair locks were measured. The measurements showed a noticeable decrease of the coefficients of friction on the treated hair locks. The treated hair locks were washed twice with a shampoo. After being sufficiently washed, the hair locks were dried, and coefficients of friction were measured again. The measurements did not reveal a significant difference from the results obtained prior to the washing. Thus it can be assumed that the obtained hair damage prevention and repair agent of Practical Example 41 can impart to hair sufficient smoothness. This property did not disappear even after the hair was shampooed.

Brushing of the agent-treated hair locks 10,000 times produced only an insignificant number of split hair (only 10% or less of those not treated with the agent). Furthermore, the obtained hair oil demonstrated a superb repair effect for split hair.

Practical Example 42

The below-given component (4) was dissolved in the below-given component (3); the obtained solution was combined and emulsified with below-given components (1) and (2); and the system was then mixed with the below-given components (5), (6), and (7). The obtained mixture was loaded into a dispenser container and thus prepared into a hair blow product.
(1) 5.0 parts by mass of decamethyl cyclopentasiloxane;
(2) 1.0 part by mass of block copolymer (A-1);
(3) 2.0 parts by mass of 1.3-butyleneglycol;
(4) 2.0 parts by mass of polyethylene (60) hard castor oil ester;
(5) 15.0 parts by mass of ethyl alcohol;
(6) 75.0 parts by mass of purified water
(7) Appropriate amount of perfume.

Practical Example 43

The below-given component (2) was dissolved in the below-given component (1); the obtained solution was combined and emulsified with below-given components (3) and (4); the system was then mixed with the below-given components (5), (6), and (7). The obtained mixture was loaded into an aerosol container equipped with a valve and thus prepared into a hair moose by adding the components (8) and (9).

(1) 20.0 parts by mass of decamethyl cyclopentasiloxane;
(2) 5.0 parts by mass of block copolymer (A-1);
(3) 5.0 parts by mass of dipropyleneglycol;
(4) 3.0 parts by mass of polyoxyethylene-modified dimethylpolysiloxane (EO 50 mass %, viscosity 100 cSt/25° C.);
(5) 10.0 parts by mass of ethanol;
(6) 51.0 parts by mass of ion-exchange water;
(7) Appropriate amount of perfume;
(8) 4.0 parts by mass of butane;
(9) 2.0 parts by mass of dimethylethyl.

Practical Example 44

The below-given components (1) to (8) were stirred and dissolved at 70° C. The solution was added to and emulsified with another solution prepared from components (9) to (12), whereby a hair cream was produced.

(1) 5.0 parts by mass of IOP (ester oil, Kokyu Alcohol Kogyo Co., Ltd.);
(2) 3.0 parts by mass of block copolymer (A-1);
(3) 5.0 parts by mass of dimethylpolysiloxane (20 cSt/25° C.);
(4) 8.0 parts by mass of tri-2-ethylhexane acid glycerin ester;
(5) 5.0 parts by mass of vaselin;
(6) 2.0 parts by mass of tearyl alcohol;
(7) 2.0 parts by mass of sorbitane monooleate;
(8) 2.0 parts by mass of polyoxyethylene hard castor oil ester (40 moles of polyoxyethylene);
(9) 5.0 parts by mass of glycerin;
(10) 5.0 parts by mass of hyaluronic acid;
(11) appropriate amount of antiseptic;
(12) balance—ion-exchange water

Practical Example 45

The below-given component (2) was dissolved in the below-given component (1); the mixture was then combined and emulsified with the below-given components (3) and (4); the emulsion was loaded into a solution of the below-given components (5) to (8), whereby a hair lotion was produced.

(1) 10.0 parts by mass of isopropyl isostearate;
(2) 3.0 parts by mass of block copolymer (A-1);
(3) 2.0 parts by mass of 1,3-butylene glycol;
(4) 2.0 parts by mass of polyoxyethylene hydrogenated castor oil ester (60 moles of polyoxyethylene);
(5) 10.0 parts by mass of titanium oxide sol (Neosunveil W-10, Catalysts & Chemical Industries, Co., Ltd.);
(6) 15.0 parts by mass of ethanol;
(7) 53.0 parts by mass of ion-exchange water;
(8) appropriate amount of perfume.

Practical Example 46

The below-given components (1) to (5) were mixed, dissolved and loaded into an aerosol container equipped with a valve. The mixture was then combined with a spray agent of the below-given components (6) and (7), whereby a hair spray was prepared.

(1) 40.0 parts by mass of light liquid paraffin (C12-15);
(2) 0.5 parts by mass of block copolymer (A-1);
(3) 2.0 parts by mass of ethanol;
(4) 10.0 parts by mass of isopropyl alcohol;
(5) appropriate amount of perfume;
(6) 7.0 parts by mass of propane;
(7) 3.0 parts by mass of dimethyl ether.

EFFECTS OF THE INVENTION

The effects of the invention consist in that the compositions for hair produced in accordance with the present invention impart to the hair such properties as the feel of moist, the feel of smoothness, thick-film touch, and ease of combing. These properties are long lasting and do not disappear after repeated brushing and drying.

Furthermore, neither in a moist state during washing, nor in a dry state, the hair produced the feel of unpleasant touch.

The hair treated with the compositions of the invention do not become sticky after drying.

The shampoo compositions of the invention demonstrated superb foamability and washability.

The effects of the compositions of the invention to impart to the hair the aforementioned properties (i.e., feel of moist, feel of smoothness, thick-film touch, ease of combing) are long lasting and cannot be easily lost even after the hair is washed.

The invention claimed is:

1. A composition for hair comprising:
a block copolymer (A) represented by the following general formula (1):

General formula (1)

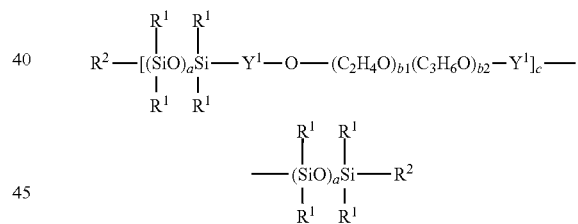

wherein $R^1$ independently designates univalent hydrocarbon groups free of aliphatic unsaturation;
$Y^1$ designates a bivalent organic group;
$R^2$ independently designates groups represented by the following formula:

(wherein $Y^2$ is a hydrogen atom or a substituted or unsubstituted univalent hydrocarbon group);
"a" is 1 or a greater integer;
"b1" is 1 or a greater integer;
"b2" is 0;
"c" is 1 or a greater integer;
the average molecular weight of the polyorganosiloxane block represented by formula:

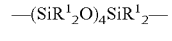

is equal to or exceeds 10,500;
the polyorganosiloxane block constitutes 50 to 99 mass % of block copolymer (A);

the average molecular weight of the polyoxyalkylene block represented by formula:

$$-(C_2H_4O)_{b1}(C_3H_6O)_{b2}-$$

is within the range of 130 to 10,000; and
the average molecular weight of block copolymer (A) is equal to or higher than 50,000; and
   a block copolymer (B) represented by the following general formula (2):

General formula (2)

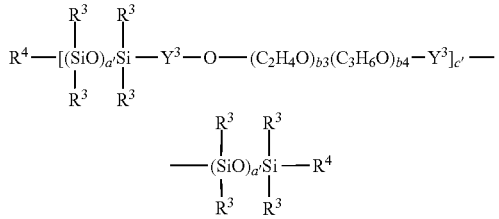

wherein $R^3$ independently designates substituted or unsubstituted univalent hydrocarbon groups
(wherein $Y^3$, b3, and b4 are defined below, $Y^4$ designates hydrogen atoms or a substituted or unsubstituted univalent hydrocarbon group);
$Y^3$ designates a bivalent organic group;
$R^4$ independently designates groups represented by the following formula:

$$-Y^3-O-(C_2H_4O)_{b3}(C_3H_6O)_{b4}-Y^4;$$

"a'" is an integer within the range of 1 to 1350;
"b3" and "b4" are, respectively, integers within the range of 1 to 220;
"c'" is an integer within the range of 1 to 50;
the average molecular weight of the polyorganosiloxane block represented by formula:

$$-(SiR^3{}_2O)_{a'}SiR^3{}_2-$$

is within the range of 134 to 10,000;
the polyorganosiloxane block constitutes 0.7 to 97.5 mass % of block copolymer (B);
the average molecular weight of the polyoxyalkylene block represented by formula:

$$-(C_2H_4O)_{b3}(C_3H_6O)_{b4}-$$

is within the range of 130 to 10,000; and
the average molecular weight of block copolymer (B) is within the range of 650 to 100,000;
   wherein each of block copolymer (A) and block copolymer (B) is present in the composition within the range of 0.01 to 10 mass % (per total weight of the composition as a reference).

2. The composition of claim 1, further comprising a silicone compound (C) of at least one type expressed by general formula (3) that is contained in an amount of 0.01 to 10 mass % (per total weight of the composition as a reference);

General formula (3)

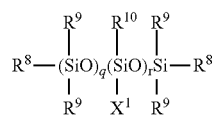

in the above formula, $R^9$ independently designates hydrogen atoms and substituted or unsubstituted univalent hydrocarbon groups; $X^1$ designates a reactive functional group represented by formula:

$$-R^{11}-Z^1$$

(where $R^{11}$ is a direct bond or a bivalent hydrocarbon group with 1 to 20 carbon atoms, and $Z^1$ is a group that contains a reactive group); $R^8$ is independently hydrogen atoms, hydroxyl groups, substituted or unsubstituted univalent hydrocarbon groups, alkoxy groups, or groups represented by $X^1$; $R^{10}$ represents either $R^9$ or $X^1$; "q" is an integer that may be at least 1; "r" is 0 or an integer that may be at least 1; and the average molecular weight of component (C) is within the range of 250 to 1,000,000.

3. The composition of claim 2, wherein in General formula (3) for silicone compound (C), $Z^1$ designates an amino-containing group or an ammonium-containing group when r=0 and at least one $R^8$ is $X^1$.

4. The composition of claim 1, further comprising a cationic surface-active agent (D) of at least one type comprising any of the compounds represented by general formulae (4), (5), and (6):

General formula (4)

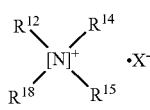

General formula (5)

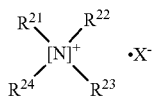

General formula (6)

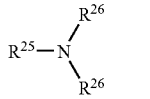

where in general formula (4), $R^{12}$ designates an alkyl group with 10 to 24 carbon atoms, hydroxyalkyl groups, acyloxyalkyl groups bonded to alkyl groups with 10 to 24 carbon atoms, or amidoalkyl groups; $R^{14}$ and $R^{15}$ independently designates benzyl groups, hydroxyalkyl groups, or alkyl groups having 1 to 3 carbon atoms; $R^{18}$ may be $R^{12}$, $R^{14}$, or $R^{15}$; and X designates a halogen atom or an alkyl sulfuric acid group;

where in general formula (5), at least one of $R^{21}$, $R^{22}$, $R^{23}$, and $R^{24}$ designates an aliphatic acryloxy(polyethoxy) ethyl group, alkenyl group, and a linear or branched alkyl group that contain 8 to 35 of total carbon atoms and can be OH-substituted or fissured by functional groups of the following formulae: —O—, —CONH—, —OCO—, or —COO—; the remaining groups may comprise hydroxyalkyl or alkyl groups with 1 to 5 carbon atoms, or polyoxyethylene groups with the total addition number not exceeding 10; $X^-$ designates a halogen ion or an organic anion; and where in general formula (6), $R^{25}$ designates an alkenyl group and a linear or branched alkyl group that contain 8 to 35 of total carbon atoms and can be OH-substituted or cleaved by functional groups of the following formulae: —O—, —CONH—, —OCO—, or —COO—; $R^{26}$ independently designates a hydroxyalkyl group, alkenyl group, or alkyl group with 1 to 22 carbon atoms.

5. The composition of claim 1, further comprising a surface-active agent (E) of at least one type selected from an anionic surface-active agent, amphoteric surface-active agent, and nonionic surface-active agent, said agent being used in an amount of 0.01 to 40 mass % (per total weight of the composition as a reference).

6. The composition of claim 1, further comprising a water-soluble polymer (F) added in an amount of 0.01 to 10 mass % (per total weight of the composition as a reference).

7. The composition of claim 1, wherein said block copolymer (A) is dissolved in a liquid cyclic silicone (G).

8. The composition of claim 1, wherein said block copolymer (A) is dissolved in a liquid chain silicone (H).

9. The composition of claim 1, wherein said block copolymer (A) is dissolved in a liquid isoparaffin-type hydrocarbon (I).

10. The composition of claim 1, wherein said block copolymer (A) is dissolved in a liquid or hard ester oil (J).

11. The composition of claim 1, comprising an emulsion type composition obtained by emulsifying a solution formed by dissolving said block copolymer (A).

12. The composition of claim 11, wherein the emulsion type composition is further compounded with 0.01 to 10 mass % (per total mass of the composition as a reference) of a water-soluble polyhydric alcohol (K).

* * * * *